(12) United States Patent  
Quirk et al.

(10) Patent No.: US 8,672,851 B1
(45) Date of Patent: Mar. 18, 2014

(54) OCULAR ULTRASOUND BASED ASSESSMENT DEVICE AND RELATED METHODS

(71) Applicant: dbMedx Inc., Littleton, CO (US)

(72) Inventors: William Quirk, Littleton, CO (US); William L. Barnard, Maple Valley, WA (US); David B. Shine, Littleton, CO (US)

(73) Assignee: dbMEDx Inc, Littleton, CO (US)

( * ) Notice: Subject to any disclaimer, the term of this patent is extended or adjusted under 35 U.S.C. 154(b) by 0 days.

(21) Appl. No.: 13/800,993

(22) Filed: Mar. 13, 2013

Related U.S. Application Data

(60) Provisional application No. 61/725,893, filed on Nov. 13, 2012.

(51) Int. Cl.
*A61B 8/14* (2006.01)

(52) U.S. Cl.
USPC .......................................... 600/459; 600/437

(58) Field of Classification Search
USPC ................................................ 600/437–469
See application file for complete search history.

(56) References Cited

U.S. PATENT DOCUMENTS

| | | | |
|---|---|---|---|
| 4,557,146 A * | 12/1985 | Buffington et al. | ............. 73/642 |
| 4,567,895 A | 2/1986 | Putzke | |
| 4,926,871 A | 5/1990 | Ganguly et al. | |
| 5,070,879 A | 12/1991 | Herres | |
| 5,699,805 A | 12/1997 | Seward et al. | |
| 6,036,646 A | 3/2000 | Barthe et al. | |
| 6,198,956 B1 | 3/2001 | Dunne | |
| 6,213,948 B1 | 4/2001 | Barthe et al. | |
| 6,378,376 B1 | 4/2002 | Derman et al. | |
| 6,626,834 B2 | 9/2003 | Dunne et al. | |
| 6,689,066 B1 | 2/2004 | Omura et al. | |

(Continued)

FOREIGN PATENT DOCUMENTS

| | | |
|---|---|---|
| WO | 2008/146203 A1 | 12/2008 |
| WO | 2011/112404 A2 | 9/2011 |

OTHER PUBLICATIONS

Extended European Search Report for European Application No. 11753817.3-2319, dated Dec. 12, 2012, 5 pages.

(Continued)

*Primary Examiner* — Sanjay Cattungal
(74) *Attorney, Agent, or Firm* — Seed IP Law Group PLLC

(57) ABSTRACT

A three-dimensional ultrasound based assessment device includes a housing having a front end, a back end, and a cavity. An ultrasonic transducer assembly can be mounted to a ball joint which is, in turn, pivotably (pitch, roll, yaw) coupled to a socket proximate the front end. A resilient or elastic sheath retains pieces forming the socket under elastic compression, with the ball pivotally retained therein. A drive assembly positioned proximate a tail or end of a stem that extends from the ball joint may be operated to sweep the ball and ultrasonic transducer. A simple interface provides at least one of a number, text, graphic, color or symbol as a visual indicator indicative of at least one of a measurement of an anatomical structure or a comparison of the measurement of the anatomical structure with a reference, without providing images of the anatomical structure.

30 Claims, 9 Drawing Sheets

(56) References Cited

U.S. PATENT DOCUMENTS

| | | |
|---|---|---|
| 7,044,737 B2 | 5/2006 | Fu |
| 8,206,307 B2 | 6/2012 | Barnard et al. |
| 8,317,711 B2 | 11/2012 | Dala-Krishna |
| 2003/0073907 A1 | 4/2003 | Taylor |
| 2007/0167813 A1 | 7/2007 | Lee et al. |
| 2009/0192389 A1* | 7/2009 | Eilers et al. .................. 600/459 |

OTHER PUBLICATIONS

Barnard et al., "Cylindrical Scanning 3-D Ultrasounds Probe," U.S. Appl. No. 61/312,363, filed Mar. 10, 2010, 6 pages.

Barnard et al., "Self Contained Ultrasound Monitoring Apparatus," U.S. Appl. No. 61/638,833, filed Apr. 26, 2012, 15 pages.

Barnard et al., "Ultrasound 3D Imaging Probe and Method," U.S. Appl. No. 61/573,493, filed Sep. 6, 2011, 56 pages.

Barnard et al., "Ultrasound Apparatus and Methods to Monitor Bodily Vessels," U.S. Appl. No. 61/638,925, filed Apr. 26, 2012, 17 pages.

Barnard et al., "Ultrasound Transducer Structure and Method of Manufacture," U.S. Appl. No. 61/621,877, filed Apr. 9, 2012, 12 pages.

Brennan et al., "Reappraisal of the Use of Inferior Vena Cava for Estimating Right Atrial Pressure," *J. Am. Soc. Echocardiography*. 20:857-861, 2007.

Shine et al., "Non-Invasive Bladder Function Assessment," U.S. Appl. No. 61/312,378, filed Mar. 10, 2010, 3 pages.

Quirk et al., "Ocular Ultrasound Based Assessment Device and Related Methods," U.S. Appl. No. 61/725,893, filed Nov. 13, 2012, 71 pages.

Barnard et al., "Oral Ultrasound Waveguide Device," U.S. Appl. No. 61/876,018, filed Sep. 9, 2013, 14 pages.

* cited by examiner

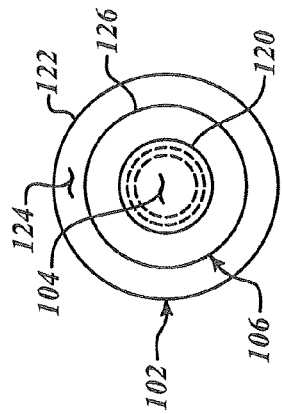
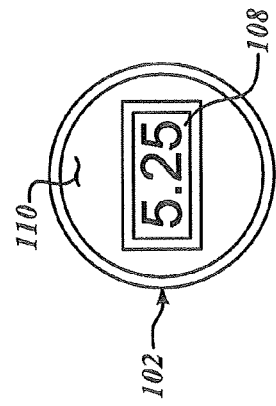
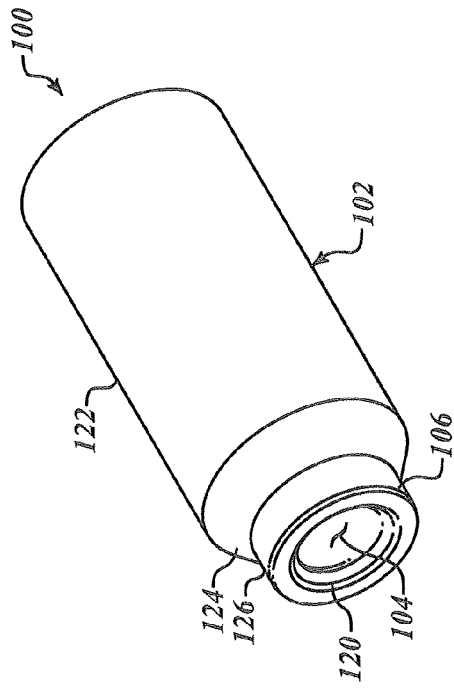
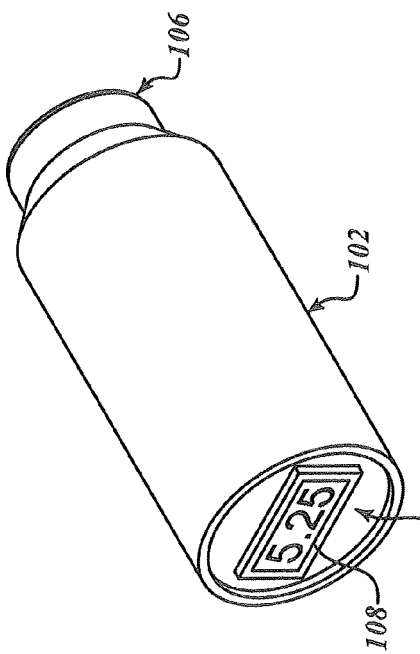

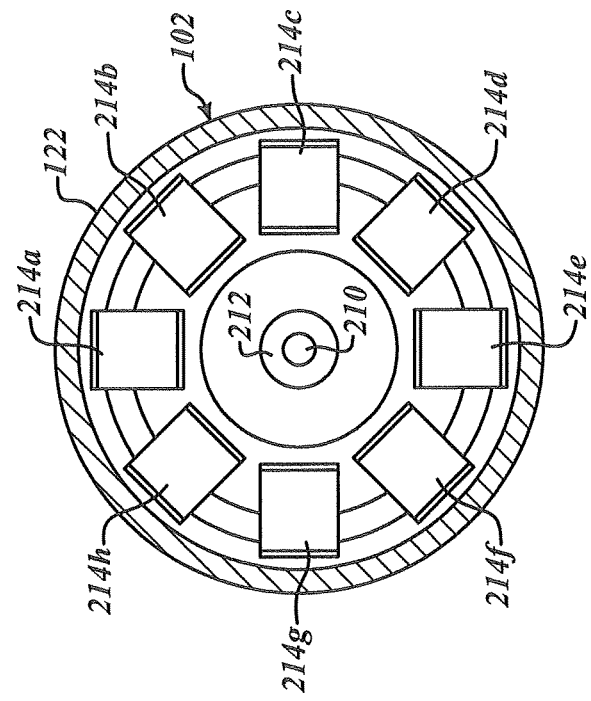
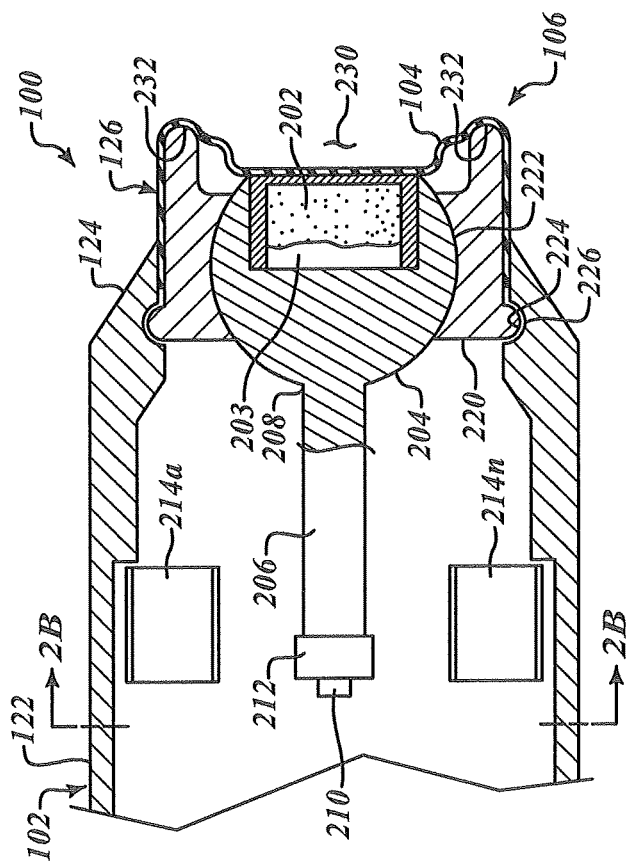

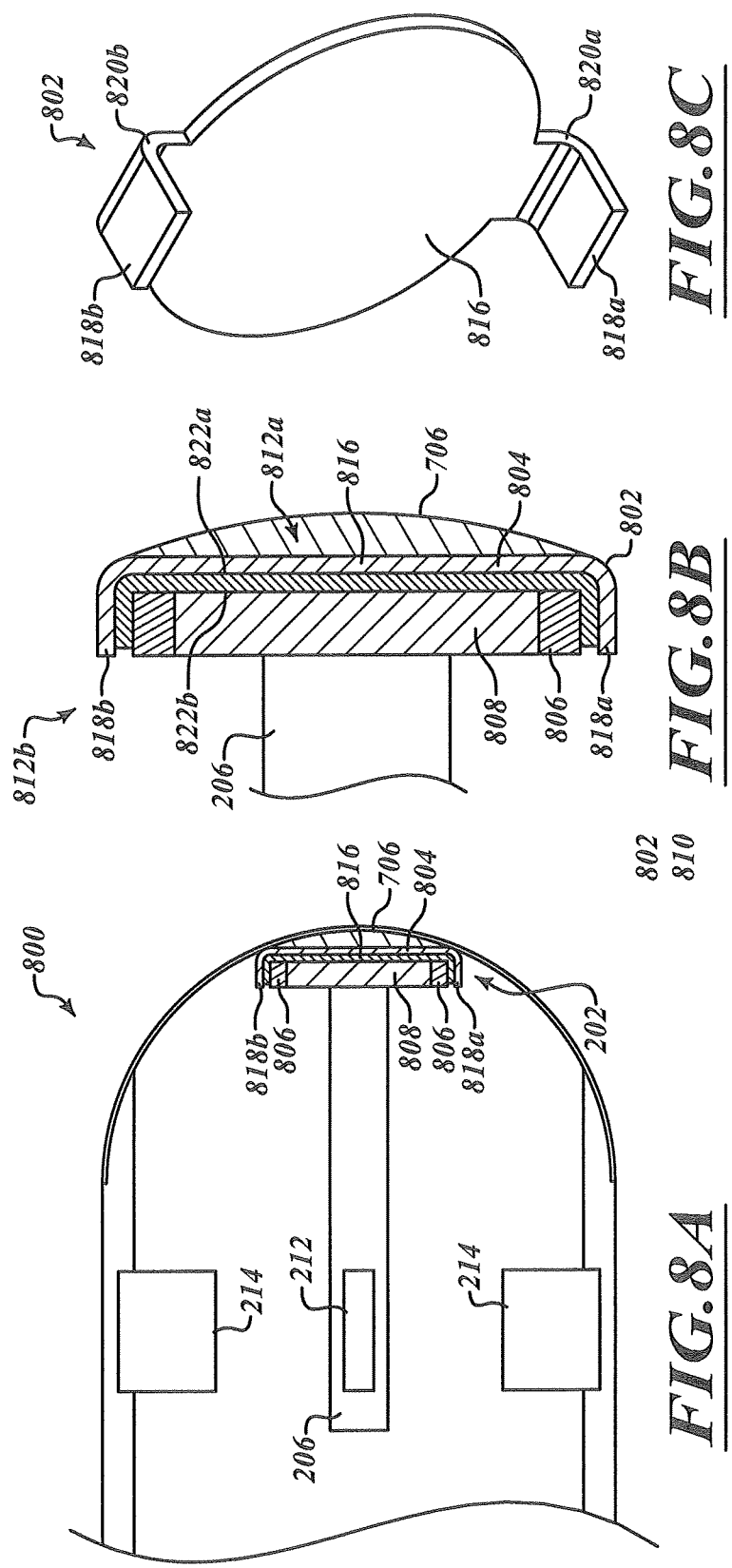

OCULAR ULTRASOUND BASED ASSESSMENT DEVICE AND RELATED METHODS

BACKGROUND

1. Technical Field

This disclosure generally relates to ultrasound devices, and more particularly to ultrasound devices having dimensional scanning capabilities and methods of using ultrasound devices for diagnostic purposes.

2. Description of the Related Art

Patients presenting at an emergency department often require assessment for elevated intracranial pressure ("EICP"), particularly as a result of head trauma or spontaneous intracranial hemorrhage. These patients often present acutely, and a diagnosis of elevated intracranial pressure suggests a serious pathology that may require rapid intervention. Typically, the diagnosis of elevated intracranial pressure is made using cranial computed tomography ("CT"). CT is a generally available but expensive imaging modality and one which exposes the patient to ionizing radiation. CT imaging typically requires a wait, while CT imaging equipment is made available to a patient, and may even require transport of the patient to the CT imaging equipment.

The use of CT in the emergency department has seen a dramatic increase in recent years, causing concern from physicians and payers (e.g., insurers) regarding excessive radiation exposure and cost associated with CT imaging. Non-contrast head CT scans are so prevalent and costly that CMS (Centers for Medicare and Medicaid Services) has initiated an imaging use efficiency metric to compare the head CT scan usage of Emergency Departments nationwide (Outpatient Measure 15, OP-15) and will use this information to identify relative head CT "over users" and reimbursement flow may be varied based on this data.

However, when faced with a patient suffering symptoms of possible elevated intracranial pressure the emergency physician or other care provider has few alternatives for positively diagnosing elevated intracranial pressure. In addition, there are situations where CT scanning may be unavailable, including combat situations, long-distance patient transportation, disaster scenes, sporting venues and any location where head trauma may occur.

BRIEF SUMMARY

Ocular ultrasonography is a relatively new application but has seen growing acceptance and provides a quick, accurate, well-tolerated, noninvasive tool for evaluating potentially vision-threatening conditions at the bedside. In addition, the eyes can often provide useful information on pathologies or disease states elsewhere in the body.

Consequently, the Applicants believe improved diagnostic ultrasound imaging devices and methods are desirable. Specifically, ocular ultrasound devices capable of measuring three dimensional structures within the eye and providing an indication of the measurement may enable a rapid detection of elevated intracranial pressure. The ocular ultrasound devices should have a small, robust form factor or package permitting their rapid deployment and use in a variety of situations from emergency room, to emergency medical services, to battlefield conditions. Such should also provide extremely simple user interfaces and handling requirements, rendering such easy to use with little or no training, even in busy, stressful and often chaotic environments.

An ultrasound based assessment device may provide for the automated sonographic measurement of the optic nerve sheath diameter, by combining a three-dimensional ultrasound scan head with integrated imaging processing to analyze the ultrasound data and provide a quantitative indication of a measurement of optic nerve sheath diameter and/or estimated intracranial pressure directly to a user.

Traditional B-scan ultrasound imaging requires a skilled user to generate and interpret the resulting two-dimensional images. Three-dimensional or "C-mode" ultrasound imaging is able to collect a broader dataset and is inherently less sensitive to operational variability than two-dimensional ultrasound imaging since the need for the system user to precisely aim the ultrasonic transducer assembly is reduced. For instance, to obtain an accurate measurement of the optic nerve sheath diameter, precise positioning of a two-dimensional ultrasound device along the widest section of the optic nerve sheath is necessary. A three-dimensional ultrasound imaging is much more forgiving of variances in aiming and is able to capture an accurate optic nerve sheath diameter measurement as long as the target falls passes through the field of view of the ultrasonic transducer assembly.

Research has demonstrated that measurement of the optic nerve sheath diameter with ultrasound can be used to detect elevated intracranial pressure in both adult and pediatric patients (Newman 2002, Blaivas 2003, Kimberly 2008). However, requiring the user to interpret two-dimensional ultrasound images assumes a trained user, as well as necessitates the expenditure of time and money to train the potential users. Requiring the user to interpret such while simultaneously obtaining the acoustic image of the optic nerve sheath may adversely affect the accuracy of the assessment of diameter, particularly under stressful conditions such as those encountered in an emergency room, or in the field.

An ultrasound based assessment device may image, measure, and/or automatically assess one or more anatomical structures such as an optic nerve sheath diameter, and which provides a direct simplified display (e.g., numeric, YES/NO, GREEN/RED) indicative of the measured optic nerve sheath diameter may address one or more of these problems. For example, an ultrasound based assessment device may provide a more accurate optic nerve sheath diameter measurement. Also for example, an ultrasound based assessment device may be operated by personnel with little or no training, even under the most stressful situations. An ultrasound based assessment device may advantageously provide such assessment with no exposure to ionizing radiation, at significantly lower cost than CT imaging, and with little or no wait. An ultrasound based assessment device is preferably provided via a small, portable, robust form, with an elegantly simple user interface.

Optic nerve sheath diameter, globe depth, globe volume, intracranial pressure, and other anatomical measurements of the eye may be non-invasively, ultrasonically measured and displayed on a simple numerical or graphical output. The clinical utility extends beyond determination of an elevated intracranial pressure condition to include such pathologies as global rupture which can be assessed using a globe depth measurement. In addition, the "cup-to-disc" ratio, a standard ophthalmic measurement of two features of the optic nerve made to evaluate glaucoma, may also be advantageously measured and displayed.

Although only a simple numerical or graphical output is provided to the user, the capability exists to wiredly (e.g., USB port) or wirelessly (e.g., IEEE 802.11 compliant radio or transceiver) transmit acoustic image data acquired by an ultrasound based assessment device to an external electronic device such as a network, desktop personal computer, tablet computer, smartphone, etc. Advantageously, the full three-dimensional ultrasound acoustic image data or an extracted two-dimensional ultrasound acoustic image data may also have utility for the remote diagnosis of the eye, for instance by a remote clinician, for other pathologies such as the presence of a tumor or other abnormal conditions. An optional recorded voice annotation or voice recognition technology may be used by the physician or system operator to orally annotate the examination or to input such things as the patient name or identification. An optional machine generated symbol reader (e.g., a one-dimensional/barcode reader, two-dimensional QR code reader, or the like) or photo image recognition (of the patient ID bracelet or chart for instance) or radio frequency identification (RFID) interrogator may also be incorporated to autonomously tag the acoustic image data. Such annotated records may be stored locally within a non-transitory storage medium or transmitted to a communicably coupled electronic device or network.

A handheld ultrasound based assessment device may be summarized as including a housing having a front end, a back end, and a cavity, the front end having an opening that opens into the cavity having a primary axis; a flexible membrane that at least in use is disposed across the opening at the front end of the housing, the flexible membrane having an inside facing surface that faces an interior of the housing and an outside facing surface that faces an exterior of the housing; an ultrasound transducer assembly having an outward face via which ultrasound signals are transmitted and received; an elongated stem having a first end and a second end received in the cavity of the housing; a first drive assembly mechanism physically coupled to the elongated stem at least proximate the second end of the elongated stem; a second drive assembly mounted within the housing at least proximate the second of the elongated stem, the first and the second drive assembly mechanisms magnetically interacting at least during use; a socket member that includes a ball joint socket located at least proximate the first end of the housing; and a ball joint from which the elongated stem extends rearwardly toward the back end of the housing, the ball joint pivotally received in the ball joint socket of the socket member, the ultrasound transducer assembly mounted to the ball joint for movement therewith.

The ultrasound transducer assembly may be adhered directly to the inside facing surface of the flexible membrane without any intervening structures. The ultrasound transducer assembly may be adhered to the inside facing surface of the flexible membrane across the entire outward face of the ultrasound transducer assembly. The flexible membrane may be a thermoplastic elastomer has at least one circular relief contour. The flexible membrane may have at least one shoulder portion proximate a radial periphery of the flexible membrane and may have a circular relief contour spaced radially inward from the shoulder. At least a portion of the outside facing surface of the flexible membrane may form a concavity. The socket member may include a first portion and a second portion, the second portion complimentary to the first portion to be physically mated thereto during assembly of the socket member. The first and the second portions of the socket member may each be composed of polyoxymethylene. The flexible membrane may physically elastically retain the first and the second portions of the socket member together. The socket member may essential be a body of revolution with a central passage, and is mounted in the opening of the housing.

The handheld ultrasound based assessment device may have a radial flange sized to be received in a groove in the opening in the housing. The elongated stem may be an integral unitary portion of at least one of the first or the second portions of the ball joint. The elongated stem and the ball joint may be composed of polyoxymethylene. The first drive assembly mechanism may include one or more permanent magnets and the second drive assembly mechanism may include at least two windings. The first drive assembly mechanism may include a single rod permanent magnet, with a first pole proximate the second end of the elongated stem and the second pole space from the second end of the elongated stem. The first drive assembly mechanism may include a single annular magnet disposed about the second end of the elongated stem, the single annular magnet having a radial polarization. The first drive assembly mechanism may include at least four annular arcuate segment magnets, each with a radial polarization distributed radially about the second end of the elongated stem. The first drive assembly mechanism may include at least eight annular arcuate segment magnets, each with a radial polarization distributed radially about the second end of the elongated stem.

The handheld ultrasound based assessment device may further include a single visual indicator device carried by the housing; and a control subsystem housed by the housing and communicatively coupled to control operation of an ultrasound transducer of the transducer assembly, and communicatively coupled to the visual indicator device and operable to cause the visual indicator device to provide at least one of a number, a text character, a graphic, a color or a symbol as a visual indicator indicative of at least one of a measurement of an anatomical structure or a comparison of the measurement of the anatomical structure with a reference, without providing any image of the anatomical structure. The visual indicator may be a number indicative of the measure of an optic nerve sheath diameter. The visual indicator may be text, color or symbol indicative of a comparison of a measure of an optic nerve sheath diameter versus a reference optic sheath diameter.

The handheld ultrasound based assessment device may further include a radio coupled to the control subsystem and operable to at least transmit information externally from the handheld ultrasound based assessment device. Such information may include the transmission of data representative of a numerical calculation, data representative of an image, or data representative of a complete three-dimensional image data set.

A method of manufacturing a handheld ultrasound based assessment device, may be summarized as including physically coupling a transducer assembly to a ball joint having an elongated stem extending therefrom and one or more magnets disposed peripherally about a distal portion of the elongated stem; locating the ball joint in a ball joint socket formed by at least two pieces of a socket member; applying a flexible membrane to elastically retain the pieces of the socket member together with the ball joint positioned in the ball joint socket and the elongated stem extending therefrom; inserting a resulting assembly of the ball joint member, the ball joint and the transducer assembly into a housing from a first end of the housing with the distal portion of the elongated stem extending rearwardly in the housing; and inserting a winding assembly into the housing from the second end to position a plurality of windings proximate the distal portion of the elongated stem.

A handheld ultrasound based assessment device may be summarized as including a housing having a front end, a back end, and a cavity, the front end having an opening that opens into the cavity having a primary axis; a flexible membrane that at least in use is disposed across the opening and positioned at the front end of the housing, the flexible membrane having an inside facing surface that faces an interior of the housing and an outside facing surface that faces an exterior of the housing; an ultrasound transducer assembly having an outward face via which ultrasound signals are transmitted and received; an elongated stem having a first end and a second end, the first end of the elongated stem extending rearwardly from the ultrasound transducer assembly in the cavity toward the back end of the housing; a first drive assembly mechanism physically coupled to the elongated stem at least proximate the second end of the elongated stem; and a second drive assembly mounted within the housing at least a portion of which is proximate the second of the elongated stem, the first and the second drive assembly mechanisms magnetically interacting at least during use, wherein the ultrasound transducer assembly is attached to the inside facing surface of the flexible membrane to conically pivot about the primary axis of the housing without any hinges or any other attachments.

A portion of the ultrasound transducer assembly may be adhered to a portion of the inside facing surface of the flexible membrane. A radial peripheral portion of the ultrasound transducer assembly may be adhered to the inside facing surface of the flexible membrane.

The handheld ultrasound based assessment device may further include an acoustic lens received between the outward face of the ultrasound transducer assembly and the flexible membrane. The flexible membrane may be an integral unitary portion of the housing. The flexible membrane may be a thermoplastic elastomer. The second drive assembly mechanism includes at least two windings. The first drive assembly mechanism may include a single rod permanent magnet, with a first pole proximate the second end of the elongated stem and the second pole space from the second end of the elongated stem. The first drive assembly mechanism may include a single annular magnet disposed about the second end of the elongated stem, the single annular magnet having a radial polarization. The first drive assembly mechanism may include at least four annular arcuate segment magnets, each with a radial polarization distributed radially about the second end of the elongated stem. The first drive assembly mechanism may include at least eight annular arcuate segment magnets, each with a radial polarization distributed radially about the second end of the elongated stem.

The handheld ultrasound based assessment device may further include a single visual indicator device carried by the housing; and a control subsystem housed by the housing and communicatively coupled to control operation of an ultrasound transducer of the transducer assembly, and communicatively coupled to the visual indicator device and operable to cause the visual indicator device to provide at least one of a number, a text character, a graphic, a color or a symbol as a visual indicator indicative of at least one of a measurement of an anatomical structure without providing any image of the anatomical structure or a comparison of the measurement of the anatomical structure with a reference. The visual indicator may be a number, text, graphic or color indicative of a measure of an optic nerve sheath diameter. The visual indicator may be a number, text, graphic or color indicative of a comparison of a measure of an optic nerve sheath diameter with a reference, for instance a measure of reference optic nerve sheath diameter.

The handheld ultrasound based assessment device may further include a radio coupled to the control subsystem and operable to at least transmit information externally from the handheld ultrasound based assessment device.

A handheld ultrasound based assessment device may be summarized as including a housing having a front end, a back end, and a cavity, the front end having an opening that opens into the cavity having a primary axis; a flexible membrane that at least in use is disposed across the opening at the front end of the housing; an ultrasound transducer assembly having a face; an elongated stem having a first end and a second end, the first end of the elongated stem extending rearwardly from the ultrasound transducer assembly in the cavity toward the back end of the housing; a first drive assembly mechanism comprising a plurality of permanent magnets disposed radially about the elongated stem at least proximate the second end; and a second drive assembly mounted comprising a plurality of windings positioned radially about the cavity and radially spaced from one another to form a passage sized to receive the second end of the elongated stem with the permanent magnets.

There may be at least eight permanent magnets disposed radially about the elongated stem. There may be at least twelve permanent magnets disposed radially about the elongated stem. The permanent magnets may be annular arcuate segment magnets, each with a radial polarization distributed radially about the second end of the elongated stem. The permanent magnets may be bar magnets distributed radially about the second end of the elongated stem, each magnet having a north pole and a south pole, all of the north poles spaced in a first radial direction that is either radially inward or radially outward and all of the south poles spaced in a second radial direction, opposite the first radial direction.

The handheld ultrasound based assessment may further include a control subsystem housed by the housing and communicatively coupled to control operation of an ultrasound transducer of the transducer assembly and communicative coupled to control a current flow through the windings.

The handheld ultrasound based assessment device may further include a single visual indicator device carried by the housing, and the control subsystem may be further communicatively coupled to the visual indicator device and operable to cause the visual indicator device to provide at least one of a number, a text character, a graphic, a color or a symbol as a visual indicator indicative of at least one of a measurement of an anatomical structure without providing any image of the anatomical structure or a comparison of the measurement of the anatomical structure with a reference. The visual indicator may be a number indicative of a measure of an optic nerve sheath diameter or of a comparison of a measure of an optic nerve sheath diameter to a reference value, without any image of the anatomical structure displayed by the control subsystem.

The handheld ultrasound based assessment device may further include a radio coupled to the control subsystem and operable to at least transmit ultrasound image data externally from the handheld ultrasound based assessment device.

A handheld ultrasound based assessment device may be summarized as including a housing having a front end, a back end, and a cavity, the front end having an opening that opens into the cavity having a primary axis; a flexible membrane that at least in use is disposed across the opening at the front end of the housing; an ultrasound transducer assembly having a face, the ultrasound transducer assembly proximate the front end; an elongated stem having a first end and a second end; a first drive assembly mechanism coupled to the elongated stem at least proximate the second end; a second drive assembly mounted within the housing; a single visual indicator device carried by the housing; and a control subsystem housed by the housing and communicatively coupled to control operation of an ultrasound transducer of the transducer assembly, communicative coupled to control a current flow through the windings, and communicatively coupled to the visual indicator device and operable to cause the visual indicator device to provide at least one of a number, a text character, a graphic, a color or a symbol as a visual indicator indicative of at least one of a measurement of an anatomical structure or a comparison of the measurement of the anatomical structure with a reference.

The control subsystem may be operable to cause the visual indicator device to provide the value indicative of the measurement of the anatomical structure without providing any image of the anatomical structure. The visual indicator may be a number indicative of a measure of an optic nerve sheath diameter. The visual indicator may be at least one of a number, a text character, a graphic, a color or a symbol indicative of a comparison of a measure of an optic nerve sheath diameter versus a reference optic sheath diameter. The visual indicator may provide a binary positive or negative indication without any additional information. The single visual indicator device may be one of a light emitting diode, an light emitting diode array, a liquid crystal diode array, or a photo-reflective dipolar electronic element array. The single visual indicator device may be positioned on the back end of the housing.

BRIEF DESCRIPTION OF THE SEVERAL VIEWS OF THE DRAWINGS

In the drawings, identical reference numbers identify similar elements or acts. The sizes and relative positions of elements in the drawings are not necessarily drawn to scale. For example, the shapes of various elements and angles are not drawn to scale, and some of these elements are arbitrarily enlarged and positioned to improve drawing legibility. Further, the particular shapes of the elements as drawn, are not intended to convey any information regarding the actual shape of the particular elements, and have been solely selected for ease of recognition in the drawings.

FIG. 1A is a perspective view of a handheld three-dimensional ultrasound based assessment device housing including an ultrasonic transducer disposed behind a flexible membrane on a front end of the housing, according to one illustrated embodiment.

FIG. 1B is an elevation view of the front end of the handheld three-dimensional ultrasound based assessment device housing shown in FIG. 1A, showing the flexible membrane on the front end of the housing, according to one illustrated embodiment.

FIG. 1C is a reverse perspective view of the handheld three-dimensional ultrasound based assessment device housing shown in FIG. 1A, including a display disposed on a back end of the housing, according to one illustrated embodiment.

FIG. 1D is an elevation view of the back end of the handheld three-dimensional ultrasound based assessment device housing shown in FIG. 1C, showing the display on the back end of the housing, according to one illustrated embodiment.

FIG. 2A is a longitudinal cross sectional view of the housing showing the relationship between a first drive assembly and a second drive assembly as well as an ultrasound transducer assembly received at least partially within a ball joint having an elongated stem extending therefrom and at least a portion of the ball joint covered by the flexible membrane; the ball joint at least partially received by a socket member, according to one illustrated embodiment.

FIG. 2B is a transverse cross-sectional view of the housing shown in FIG. 2A taken along line 2B-2B that shows the relationship between the first drive assembly positioned on the elongated stem disposed longitudinally within the housing and the second drive assembly disposed within the interior portion of the housing, according to one illustrated embodiment.

FIG. 8A is a partial cross section of an example ultrasonic transducer assembly disposed within a handheld three-dimensional ultrasound based assessment device, according to one illustrated embodiment.

FIG. 8B is an enlarged cross section showing the ultrasonic transducer assembly shown in FIG. 8A, according to one illustrated embodiment.

FIG. 8C is a perspective view of an example frame used in the ultrasonic transducer assembly shown in FIG. 8A, according to one illustrated embodiment.

DETAILED DESCRIPTION

Figure 3:
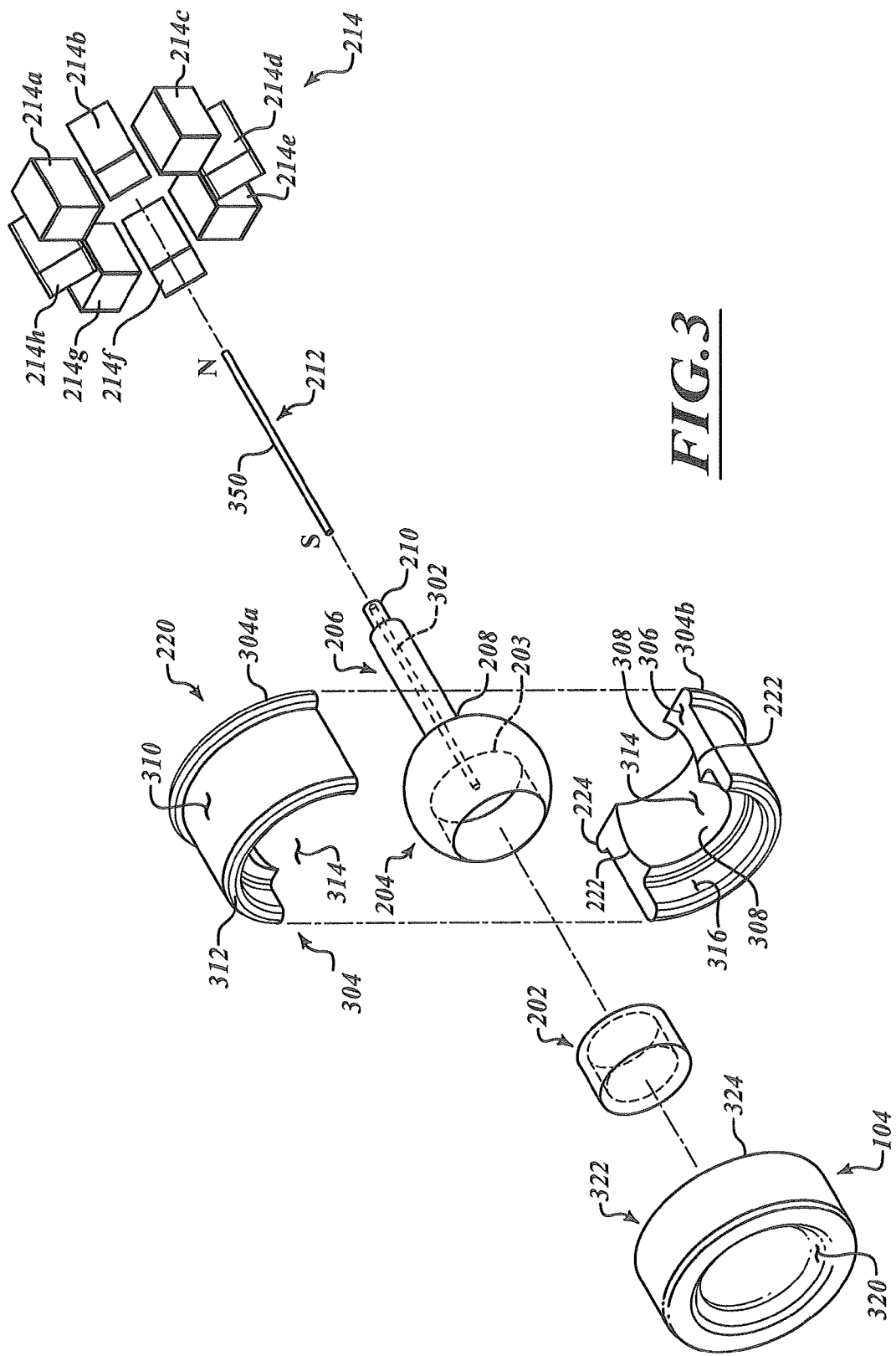
FIG. 3 is an exploded view diagram showing the relationship between an ultrasonic transducer assembly, a ball joint, a multi-piece socket assembly, a flexible membrane, a first drive assembly, and a second drive assembly, according to one illustrated embodiment.

In the following description, certain specific details are set forth in order to provide a thorough understanding of various disclosed embodiments. However, one skilled in the relevant art will recognize that embodiments may be practiced without one or more of these specific details, or with other methods, components, materials, etc. In other instances, well-known anatomical structures and structures associated with ultrasound systems and transducers have not been shown or described in detail to avoid unnecessarily obscuring descriptions of the embodiments.

Unless the context requires otherwise, throughout the specification and claims which follow, the word "comprise" and variations thereof, such as, "comprises" and "comprising" are to be construed in an open, inclusive sense, that is as "including, but not limited to."

Reference throughout this specification to "one embodiment" or "an embodiment" means that a particular feature, structure or characteristic described in connection with the embodiment is included in at least one embodiment. Thus, the appearances of the phrases "in one embodiment" or "in an embodiment" in various places throughout this specification are not necessarily all referring to the same embodiment. Furthermore, the particular features, structures, or characteristics may be combined in any suitable manner in one or more embodiments.

As used in this specification and the appended claims, the singular forms "a," "an," and "the" include plural referents unless the content clearly dictates otherwise. It should also be noted that the term "or" is generally employed in its sense including "and/or" unless the content clearly dictates otherwise.

The headings and Abstract of the Disclosure provided herein are for convenience only and do not interpret the scope or meaning of the embodiments.

FIGS. 1A-1D show a handheld three-dimensional ultrasound based assessment device 100 that can be used to quickly and accurately obtain three-dimensional acoustic image data from which one or more dimensional measurements of a target can be obtained. The three-dimensional ultrasound based assessment device 100 includes a housing 102 having a cavity formed therein, an ultrasonic transducer assembly (not visible in FIGS. 1A-1D) is disposed adjacent an inside facing surface of a flexible membrane 104 positioned on a front end 106 of the housing, and a display 108 may be optionally positioned on a back end 110 of the housing.

A user can obtain the one or more dimensional measurements by placing the front end 106 of the three-dimensional ultrasound based assessment device 100 proximate the subject and activating the ultrasound based assessment device 100. For example, an acoustic image and data relevant to the optical nerve sheath diameter or globe depth of a subject may be obtained by placing the optical three-dimensional ultrasound based assessment device 100 on the exterior surface of the subject's eyelid. The three-dimensional ultrasound based assessment device 100 can be easily positioned by the system operator in a position that is parallel with the line of vision or optical axis of the eye. Controls within the three-dimensional ultrasound based assessment device 100 activate and sweep the ultrasonic transducer assembly across the target area to autonomously collect three-dimensional acoustic image data that includes information representative of the target without requiring movement of the device by the system user. Image processing performed within the three-dimensional ultrasound based assessment device 100 can obtain one or more dimensional measurements from the acquired acoustic image data and communicate to the user an indication (e.g., number, text, graphic, color) of the dimensional measurements or a comparison of the dimensional measurements to a reference, for example via the display 108 on the back end 110 of the three-dimensional ultrasound based assessment device 100.

FIG. 1A provides a perspective view of the front end 106 of the three-dimensional ultrasound based assessment device 100 that shows the general concave shape formed by an outside facing surface of a flexible membrane 104 extending across at least a portion of the front end 106. FIG. 1B provides an elevation view of the front end 106 of the housing showing the outside facing surface including one or more circular relief contours 120 formed in the flexible membrane 104. The flexible membrane 104 provides a continuous, fluidly impermeable, resilient covering extending across some or all of the exposed portions of the ultrasonic transducer assembly. The one or more relief contours 120 may include, but are not limited to any number of folds, pleats, ridges, shoulders, diaphragms, or similar continuous or discontinuous features capable of facilitating the three-dimensional movement or displacement of the flexible membrane 104 in response to movement of the ultrasonic transducer assembly proximate at least a portion of an inside facing surface of the flexible membrane 104.

Also visible in FIG. 1A is an example overall structure of the housing 102. Although the housing 102 is depicted as a cylindrical tubular member in FIGS. 1A-1D, virtually any physical size, shape or configuration may be similarly employed. All or a portion of the housing 102 may be hollow, forming a cavity therein. In at least one instance, the housing 102 may include a hollow cylindrical tubular section 122 that terminates in a hollow frustum section 124 coaxially disposed along a shared primary axis. In at least some instances, an assembly 126 is inserted at least partially in the cavity existent in the cylindrical tubular section 122 or the frustum section 124. In at least some instances, the assembly 126 can include a pivotable ultrasonic transducer assembly. Such a construction advantageously permits the placement of driver and control electronics proximate the back end 110 of the cylindrical section 122 while the sound beam generated by the ultrasonic transducer assembly exits the front end 106 of the three-dimensional ultrasound based assessment device 100. The smaller ultrasonic transducer assembly is advantageously disposed at the front end 106 of the device where it may be more easily placed proximate an external surface (e.g., a closed eyelid) of the subject. It should be understood that other configurations incorporating similar features may be used with equal effectiveness, however for clarity and ease of discussion, a cylindrical tubular shaped housing 102 having the general layout and configuration depicted in FIGS. 1A-1D is used consistently herein.

The housing 102 can include any structure into which an ultrasonic transducer and the associated transducer drive, control, and image processing electronics can be at least partially fitted. A hollow cylindrically tubular shaped housing 102 is easy to manufacture, mechanically robust, and provides a convenient, easily handled vessel in which to house the ultrasonic transducer assembly and associated electronics and controls. The cylindrical shape also limits the number of edges which might otherwise present a source of discomfort or even injury to a subject or system user. All or a portion of the housing 102 may be of a material that is acoustically transparent and in some embodiments optically transparent or translucent. For example, the housing 102 may be an acoustically and optically transparent thermoplastic elastomer, such as, for example, a material available from Arkema Inc. under the name PEBAX®. Alternatively, the housing 102 may be of an acrylic or another plastic material, metal, or a combination thereof.

In some instances, the housing 102 may include a plurality of sections that are held together using one or more devices, fixtures, or structures such as threads, snaps, grooves, detents, or comparable attachment features to permit at least a partial disassembly and reassembly of the housing 102. Such disassembly can allow access to at least a portion of the cavity within the housing 102. Such access may permit, for example, replacement of a power source (e.g., batteries) for the ultrasonic transducer assembly, or access to a nontransitory storage device such as a removable data storage card that is used by the three-dimensional ultrasound based assessment device 100 to store one or more machine executable instruction sets, acquired acoustic image data, related audio or machine readable code data, or the like.

In some instances, the housing 102 may have one or more seals or similar components, structures, or the like to prevent the ingress of water or other liquids into the cavity within the housing 102. In some instances, all or a portion of the housing 102 may be of construction and materials permitting the thermal or chemical sterilization of all or a portion of the exterior surface of the three-dimensional ultrasound based assessment device 100. The three-dimensional ultrasound based assessment device 100 may be activated by a switch (not shown in FIGS. 1A-1D), such as a push button switch, positioned on an end or side of the housing 102. As another example, the switch may be a wireless switch, such as, for example, a hall effect switch, that allows activation of the device 100 without electrical connections or components of the switch penetrating the hollow interior portion of the housing 102.

In at least some situations, the three-dimensional ultrasound based assessment device 100 may be manually operated, obtaining a three-dimensional acoustic image of a target area and optionally displaying results on the display 108 when one or more manual controls such as a switch or similar device activated by the system user. In other situations, the three-dimensional ultrasound based assessment device 100 may operate autonomously, for example through the use of a proximity or conductivity sensor able to detect when the front end 106 of the device 100 is placed proximate a subject. In such instances, the proximity or similar sensor may provide one or more signals to capable of placing the device in an ON or AWAKE state or mode in which three-dimensional acoustic image data of the target is obtained and results are optionally displayed on the display 118.

FIG. 1C provides a perspective view of the back end 110 of the three-dimensional ultrasound based assessment device 100. FIG. 1D provides an elevation view of the back end 110 of the housing 102 showing the optional display 108. Although shown as a numeric display, the display 108 may include any type of display or similar indicator capable of conveying measurement information obtained by the three-dimensional ultrasound based assessment device 100 or other information indicative of results based on the measurements. In some instances all or a portion of the display 108 may include a single or multi-color graphic presentation of measurement data, without ultrasound images. For example, the display 108 may indicate one or more dimensional measurements (e.g., optic nerve sheath diameter) or the presence of one or more defined conditions (e.g., elevated intracranial pressure) in the form of a number (e.g., 5.5), text (e.g., YES, NO), color (e.g., GREEN, RED, AMBER), graphic (e.g., SMILE, FROWN), or symbol (e.g., CIRCLE, CIRCLE with CROSS) based at least in part on the acoustic image data obtained by the three-dimensional ultrasound based assessment device 100. In some implementations, the display 108 may be a simple single or multi-color light emitting diode or LED indicator that conveys the measurement as either within (e.g., GREEN) or outside (e.g., RED) of acceptable limits, or on the margin of acceptable limits (e.g., YELLOW or AMBER). In other implementations, the display 108 can be an externally illuminated display (e.g., a liquid crystal or "LCD" display) or a self-illuminated display (e.g., a backlit LCD display or an LED display). In either implementation, the indication may be of an absolute measurement, or may be of a comparison of the absolute measurement with or to some reference (e.g., measurement of reference optic nerve sheath diameter, without displaying the ultrasound images or image information from which the measurement was measured.

When used in ophthalmologic applications, the displayed indication may include, but is not limited to the numeric measurement of optic nerve sheath diameter, for instance in millimeters (mm). Research has indicated that an average optic nerve sheath diameter of greater than 5 mm in adults, greater than 4.5 mm in children and greater than 4.0 mm in infants less than 1 year old has been correlated with elevated intracranial pressure both directly and indirectly (Newman 2002, Blaivas 2003, Kimberly 2008). Thus the measurement of optic nerve sheath diameter by the three-dimensional ultrasound based assessment device 100 may advantageously provide attending personnel with an indication of whether a subject may be suffering from elevated intracranial pressure without the need for a costly CT. Additionally, the handheld three-dimensional ultrasound based assessment device 100 may advantageously be used to measure the optic nerve sheath diameter of a subject to provide a rapid, reliable indication of elevated intracranial pressure in situations where the use of CT is either impossible or inadvisable.

In addition to providing an indication of measurement, in at least some instances the display 108 may also be used to visually convey system related information. For example, the display 108 may variously display a visible indication of the quantity of power remaining in the power source, the quantity of nontransitory storage media (i.e., "memory") remaining, system fault or diagnostic data (e.g., inability to acquire the measurement due to improper positioning of the device 100), or combinations thereof.

In some instances, the display 108 can function as both an input and an output device. For example, the display 108 may include one or more membrane switches, one or more capacitive switches, one or more resistive switches, or combinations thereof. Such switches may be useful for a user to provide the device with an input indicative of target biometric data such as: age, weight, physical size, or the like. In some instances, all or a portion of the display 108 may include a capacitive or resistive touch sensitive input region (i.e., a touchscreen).

In addition to providing a visible display of measurement data, in at least some instances the display 108 may also provide an audible indication of measurement or other data which may include sounds (e.g., a distinctive beeps or patterns of beeps indicative of measurements within or outside of acceptable limits), voice prompts (e.g., "reposition device" in response to the device's inability to obtain a measurement), or combinations thereof.

FIG. 2A is a partial longitudinal sectional view of the front end 106 of the three-dimensional ultrasound based assessment device 100. FIG. 2B is a transverse cross-sectional view of the three-dimensional ultrasound based assessment device 100 taken along cut line 2B-2B in FIG. 2A. Visible in FIG. 2A is the ultrasonic transducer assembly 202 from which the ultrasonic signals are transmitted and received. The ultrasonic transducer assembly 202 is at least partially received in a recess or similar cavity 203 formed within a ball joint 204. An elongated stem 206 extending from the ball joint 204 is coupled at a first end 208 to the ball joint 204. A first drive assembly 212 is coupled to the elongated stem 206, at, near, or proximate a second end 210 of the elongated stem 206.

A second drive assembly 214a-214n (collectively "second drive assembly 214") comprising any number of devices capable of individually or collectively creating a magnetic field of desirable shape and intensity is mounted within the housing 102 at least proximate the second end 210 of the elongated stem 206. During operation, the interaction of a magnetic field created by the first drive assembly 212 with a magnetic field created by the second drive assembly 214 causes a displacement of the elongated stem 206, the ball joint 204 and the ultrasonic transducer assembly 202. The ultrasonic transducer assembly 202 is shown and described in greater detail in FIGS. 8A and 8B below.

A single or multi-piece socket member 220 including a ball joint socket 222 pivotably receives and retains the ball joint 204. The socket member 220 is retained within the front end 106 of the housing 102 by one or more fasteners or retention devices. For example, the socket member 220 may be retained in the front end 106 of the housing 102 using a continuous or discontinuous radial flange 224 extending continuously or discontinuously about a perimeter of all or a portion of the exterior surface of the socket member 220. The radial flange 224 may be received in a corresponding continuous or discontinuous groove 226 formed on the interior surface of the hollow cylindrical 122 or frustum 124 portions of the housing 102 when the socket member 220 is inserted into the first end 106 of the housing 102. In at least some instances, all or a portion of the socket member 220 can project or otherwise longitudinally extend from the first end 106, along the primary axis of the housing 102 forming at least a portion of the assembly 126. In at least some instances, a continuous or discontinuous shoulder 232 formed parallel to the primary axis of the device 100 can extend from the portion of the socket member 220 projecting from the housing 102. In at least some instances, the shoulder 232 projecting from the socket member 220 can form a generally concave region 230, at least a portion of which can include the face of the ultrasonic transducer assembly 202.

The ultrasonic transducer assembly 202 is coupled to at least a portion of the ball joint 204. Mounting the ultrasonic transducer assembly 202 to the ball joint advantageously permits the ultrasonic transducer assembly 202 to pivot in conjunction with the ball joint 204. In at least some instances, the ultrasonic transducer assembly 202 can be at least partially received within a recess or similar cavity 203 formed in the ball joint 204. The ball joint 204 may be machined or cast from any material. Preferably, the ball joint 204 is formed from any current or future self lubricating material capable of withstanding the motion of the ball joint 204 within the socket member 220 during normal operation. Example self lubricating materials include, but are not limited to: polyoxymethylene (marketed by DuPont® under the tradename Delrin®), ultra-high molecular weight polyethylene (UHMW-PE marketed by Quadrant® under the trade name Tivar®), polytetrafluoroethylene (PTFE marketed by DuPont® under the tradename Teflon®), or similar. The ball joint 204 can have a diameter of from about 5 mm to about 30 mm; from about 10 mm to about 25 mm; or from about 10 mm to about 20 mm.

In at least some instances, the ball joint 204 can be in the physical form of a truncated sphere or spheroid with the ultrasonic transducer assembly 202 received in a cavity 203 formed normal (i.e., at a 90° angle) to the flat portion of the truncated sphere or spheroid. In at least some instances, the "face" or portion of the ultrasonic transducer assembly 202 that emits and receives ultrasonic energy can be parallel to the flat portion of the truncated sphere or spheroid ball joint 204. In some instances, some or all of the "face" or portion of the ultrasonic transducer assembly 202 capable of emitting and receiving ultrasonic energy can be coplanar with the flat portion of the truncated sphere or spheroid ball joint 204. In such instances, the elongated stem 206 can extend radially outward from the ball joint 204, in a direction 180° opposed to the flat portion of the truncated sphere or spheroid.

In some instances, the elongated stem 206 may be cast, machined or otherwise formed with all or a portion of the ball joint 204. In other instances, the elongated stem 206 may be formed separate from the ball joint 204 and the first end 208 of the elongated stem 206 may be attached to the ball joint 204 using an adhesive, a threaded connection, a friction fit, or any combination thereof. For example, male threads may be formed on the exterior of at least a portion of the first end 208 of the elongated stem 206 and complimentary female threads may be formed on an interior surface of a cavity formed in the ball joint 204 to permit a threaded physical coupling of the elongated stem 206 to the ball joint 204. In another instance, the elongated stem 206 can be chemically or thermally welded or otherwise fused to the ball joint 204.

The elongated stem 206 can be of any length and cross section. For example, in some instances, the elongated stem 206 can have a length of from about 10 mm to about 40 mm and a circular cross section having a diameter of from about 3 mm to about 8 mm. Elongated stems 206 having a square cross section, a rectangular cross section, a triangular cross section, an oval cross section, or any other cross section may be substituted. In some instances, the elongated stem 206 can have an unvarying single cross sectional profile between the first end 208 and the second end 210. In other instances, the elongated stem 206 can have a variable cross sectional profile between the first end and the second end 210. For example to accommodate the physical coupling of the first drive assembly 212 to at least a portion of the elongated stem 206. The elongated stem 206 shown in FIGS. 2A and 2B has a generally circular cross sectional profile having a first diameter at the first end 208 and a generally circular cross sectional profile having a second diameter that is less than the first diameter at the second end 210.

In some instances, a channel or conduit (not shown in FIG. 2A or 2B) may extend axially through the elongated stem 206. A channel or conduit may be similarly routed through at least a portion of the ball joint 204. In at least some instances, the channel or conduit can be routed coaxially with the longitudinal axis of the elongated stem 206. In other instances, the channel or conduit can be routed parallel to the longitudinal axis of the elongated stem 206. One or more conductors conductively coupled to the ultrasonic transducer assembly 202 may be routed via the channel to conduit from the ultrasonic transducer assembly 202 to one or more electrical systems or devices disposed within the cavity in the housing 102.

The first drive assembly 212 is disposed proximate the second end 210 of the elongated stem 206. The first drive assembly 212 can include any number of devices, systems, or combination of systems and devices capable of generating a magnetic field extending at least radially outward from the second end 210 of the elongated stem 212. In at least some instances, devices producing a magnetic field and suitable for use in the first drive assembly 212 can include, but are not limited to, any number of metallic, rare-earth, or composite permanent magnets, and similar permanently magnetized materials. In other instances, devices producing a magnetic field and suitable for use in the first drive assembly 212 can include, but are not limited to, any number of electromagnets, coils, inductors, windings, and similar electrically generated magnetic field producing devices. As shown in FIGS. 2A and 2B, in some instances the first drive assembly 210 can include a permanent toroidal magnet or a toroidal coil or winding through which at least a portion of the second end 210 of the elongated stem 206 may be passed. Other first drive assembly 212 configurations are shown in FIGS. 4A-4D and are discussed in greater detail below.

The distance separating the first drive assembly 212 and the ultrasonic transducer assembly 202 is generally quite small (i.e., on the order of 10 millimeters to 50 millimeters). Consequently, only a small range of motion of the first drive assembly 212 is needed to provide a reasonably large cone of coverage for the ultrasonic transducer assembly 202 as the ball joint 204 containing the ultrasonic transducer assembly 202 pivots within the socket member 220. The first drive assembly 212 may be positioned at a distance of from about 10 millimeters to about 50 millimeters from the face of the ultrasonic transducer 202; from about 10 millimeters to about 40 millimeters from the face of the ultrasonic transducer 202; from about 10 millimeters to about 30 millimeters from the face of the ultrasonic transducer 202; or from about 10 millimeters to about 20 millimeters from the face of the ultrasonic transducer 202. In at least one instance, the first drive assembly 212 can be positioned approximately 15 millimeters from the face of the ultrasonic transducer.

The second drive assembly 214 may be disposed in a symmetric or asymmetric pattern within the housing 102, proximate the second end 210 of the elongated stem 206. In at least some instances, devices producing a magnetic field and suitable for use in the second drive assembly 214 can include, but are not limited to, any number of metallic, rare-earth, or composite permanent magnets, and similar permanently magnetized materials. In other instances, devices producing a magnetic field and suitable for use in the second drive assembly 214 can include, but are not limited to, any number of electromagnets, coils, inductors, windings, and similar electrically generated magnetic field producing devices. As shown in FIGS. 2A and 2B, in some instances the second drive assembly 214 can include a number of coils, windings or similar electrically generated magnetic field producing devices disposed in the housing 102 proximate the second end 210 of the elongated stem 206 (eight such coils or windings, labeled 214a-214h are shown in FIG. 2B). Other second drive assembly 214 configurations are possible.

The magnetic field generated by the second drive assembly 214 is sufficient to displace the first drive assembly 212 coupled to the elongated stem 206. As the first drive assembly 212 is displaced by the magnetic field generated by the second drive assembly 214, the displacement is translated via the elongated stem 206 to the ball joint 204 and ultrasonic transducer assembly 202. Advantageously, the ultrasonic energy emitted by the ultrasonic transducer assembly 202 can be projected from the front end 106 of the housing 102 in any desired pattern (e.g., a conical pattern) by controlling the movement of the first drive assembly 212 and consequently the ultrasonic transducer assembly 202 that is physically coupled thereto. By controlling the position of the first drive assembly 212 within the magnetic field generated by the second drive assembly 214, data representative of three-dimensional acoustic image of the target may be obtained.

The range of motion through which the ultrasonic transducer assembly 202 may be swept influences the overall level of accuracy and detail present in the three-dimensional acoustic image of the target. The ultrasonic transducer assembly 202 is physically coupled to the first drive assembly 212 and thus, the range of motion of the ultrasonic transducer assembly 202 is related to the range of motion achievable with the first drive assembly 212. The range of motion of the first drive assembly 212 is related to the size, type, and number of magnetic structures provided by the second drive assembly 214. Although the second drive assembly 214 includes eight coils or windings in FIG. 2B, any number of structures (e.g., 2, 4, 12, 16, etc.) may be disposed proximate the second end 210 of the elongated stem 206. By controlling both the shape and intensity of the magnetic field generated by the second drive assembly 214, the first drive assembly 212 may be positioned in any location within the region bordered by the second drive assembly 214.

In at least one instance, the first drive assembly 212 can include one or more permanent magnets and the second drive assembly 214 can include a number of coils or windings, each individually coupled to a power supply. The flow of current to each of the number of coils or windings in the second drive assembly 214 can be individually controlled by one or more controllers (not shown in FIGS. 2A and 2B). The shape and intensity of the composite magnetic field generated by each of the respective coils or windings in the second drive assembly 214 controls the movement and position of the first drive assembly 212 and consequently the coverage of the beam pattern of ultrasonic energy produced by the ultrasonic transducer assembly 202. Advantageously, by selectively altering or adjusting the current flow to each of the number of electromagnets in the second drive assembly 214 any number of coverage patterns may be generated.

In at least one instance, the current flow to each of the number of electromagnets in the second drive assembly 214 is pulse width modulated at a frequency (e.g., in excess of 1 MHz) that is greater than the desired sweep speed of the ultrasonic transducer 202. In at least some instances, positional feedback containing data indicative of the position or movement of the first drive assembly 212 may be provided to the controller via a number of non-energized magnetic field producing devices in the second drive assembly 214.

FIG. 3 is an exploded view showing the assembly of an illustrative ball joint 204 with an integrally formed elongated stem 206, a multi-piece socket member 220, a flexible member 104, a first drive assembly 212, and a second drive assembly 214. In at least some situations, the three-dimensional ultrasonic scanner 100 may be assembled by inserting the ultrasonic transducer assembly at least partially within the cavity 203 formed in the ball joint 204 and trapping the ball joint 204 between pieces of the multi-piece socket assembly 220. The assembly continues by placing the assembled multi-piece socket assembly 220 into the inside portion of the flexible member 104. The flexible member 104 exerts a compressive force on the multi-piece socket member 220 that holds the pieces forming the multi-piece socket member 220 together and traps the ball joint 204 and ultrasonic transducer assembly 202 within the ball joint socket 222. A first drive assembly in the form of a bar magnet 402 is placed in, on, or about at least a portion of the elongated stem 206.

The elongated stem 206 is shown attached to the ball joint 204 at a point 180° opposed to the face of the ultrasonic transducer assembly 202. The elongated stem 206 features a reduced diameter second end 210 distal from the ball joint 204. The reduced diameter second end 210 can receive and couple to the first drive assembly 212. The first drive assembly 212 may be physically coupled to the elongated stem 206 using an adhesive, a threaded fastener, a compression fit, a friction fit, or any combination thereof. In some instances, the second end 210 of the elongated stem 206 can be mechanically flared or thermally expanded after the installation of the first drive assembly 212 to physically retain the first drive assembly 212 on the elongated stem 206.

The channel or conduit 302 through which the conductors coupled to the ultrasonic transducer 202 pass is shown passing through both the ball joint 204 and the elongated stem 206 along the primary axis of the elongated stem 206.

The assembled pieces of the multi-piece socket member 220 form a ball joint socket 222 which traps the ball joint 204 therein. Although the socket member 220 shown in FIG. 3 includes only two pieces 304a-304b (collectively "socket member pieces 304'"), any number of constituent component pieces may be used to form the socket member 220. By assembling the socket member pieces 304 about the ball joint 204, the ball joint 204 can be securely trapped within the ball joint socket 222. In at least some instances, the mating surfaces 306 of the individual pieces forming the socket member 220 may be machined, planed, or otherwise surface finished such that the socket member pieces 304 fit together without gaps to provide a smooth ball joint socket 222 surface 308. In at least some instances, the assembled socket member pieces 304 may also provide a smooth, continuous exterior surface 308.

The longitudinal, convex, shoulder 232 extends from all or a portion of the socket member 220. In at least one instance, a continuous convex shoulder 232 can extend longitudinally outward along the perimeter of the portion of the socket member 220 projecting from the first end 106 of the housing 102. The convex shoulder 232 extending from the socket member 220 forms the periphery of the generally concave region 230 on the exposed face 316 of the socket member 220.

The flexible membrane 104 has an outside facing surface 320 and an inside facing surface 322 (not visible in FIG. 3). The flexible membrane 104 has a generally cup shaped appearance with a lip 324 forming an opening or orifice into which the socket member 220 may be inserted. In at least some instances, the flexible membrane 104 can be snugly fitted to the smooth, continuous exterior surface 308 of the assembled socket member pieces 304 such that the compressive force applied by the flexible membrane 104 to the assembled socket member pieces 304 is sufficient to retain the assembled socket member pieces 304 in position. By maintaining the socket member pieces 304 in position, the ball joint 204 and ultrasonic transducer assembly 202 are pivotably trapped within the ball joint socket 222 formed by the assembled socket member pieces 304.

When placed over the assembled socket member pieces 304, the elastomeric nature of the flexible membrane 104 beneficially compresses the socket member pieces 304. By compressing the assembled socket member pieces 304, the assembled pieces are held in contact with each other and the ball joint 204 is pivotably trapped within the ball joint socket 222 formed by the assembled socket member pieces 304. The smooth exterior surface 308 formed by the assembled socket member pieces 304 and the presence of a smooth radius rather than sharp corners on the shoulder 312 portion of assembled socket member pieces 304 beneficially reduces the likelihood of damage such as perforations or tears in the flexible membrane 104. Additionally, the use of the flexible membrane 104 permits the assembly of the socket member pieces 304, the ball joint 204, and the ultrasonic transducer assembly 202 prior to insertion of the assembled components into the flexible membrane 104.

After insertion of the assembled socket member pieces 304 into the flexible membrane 104 the flexible membrane covered socket member 220 can be inserted into the housing 102. Inserting at least a portion of the flexible membrane covered socket member 220 into the housing may trap at least a portion of the flexible membrane lip 324 between the exterior surface 308 of the socket member 220 and the interior surface of the cavity in housing 102. Trapping the flexible membrane 104 between the socket member 220 and the housing 102 permits the flexible membrane 104 to serve as a seal preventing the ingress of liquids through the gap between the socket member 220 and the housing 102. Additionally, by trapping the flexible membrane 104 between the socket member 220 and the housing 102, the flexible member 104 is securely retained on the socket member 220 and is maintained in close contact with both the ultrasonic transducer 202 and the ball joint 204.

The flexible membrane 104 can include any liquid impermeable, thermoplastic elastomer. In some instances, the flexible membrane 104 can be a continuous membrane, passing partially or completely across the face of the ultrasonic transducer assembly 202. In other instances, one or more apertures or similar voids may be formed within the flexible membrane 104 such that upon insertion of the assembled socket member pieces 304, at least a portion of the ultrasonic transducer assembly face is exposed, i.e., not proximate the inside facing surface 322 of the flexible member 104.

Preferably, the flexible membrane 104 should be acoustically transparent, causing little or no attenuation or other deleterious effect on the beam of sound that is emitted and received by the ultrasonic transducer assembly 202. In at least some instances, the flexible membrane 104 can be partially or entirely formed using a thermoplastic elastomer ("TPE") such as styrenic block copolymers, polyolefin blends, elastomeric alloys, thermoplastic polyurethanes, thermoplastic copolyester, or thermoplastic polyamides. Example TPE products that come from block copolymers group include, but are not limited to: Styroflex® (manufactured by BASF), Kraton® (manufactured by Shell Chemicals), Pellethane® and Engage® (manufactured by Dow chemical), Pebax® (manufactured by Arkema), Arnitel® (manufactured by DSM), Hytrel® (manufactured by DuPont) and more. TPEs may also include one or more elastomer alloys, including but not limited to: Dryflex®, Mediprene®, Santoprene®, Geolast® (manufactured by Monsanto), Sarlink® (manufactured by DSM), Forprene®, Alcryn® (manufactured by DuPont) and Evoprene® (manufactured by AlphaGary).

The flexible, elastomeric nature of the flexible membrane 104 permits the flexible membrane 104 to closely follow, conform or mold to the underlying structure of the socket member 220, ball joint 204 and ultrasonic transducer assembly 202 that are in contact with the inside facing surface 322 of the flexible membrane 104. In particular, the flexible membrane 104 can closely follow the generally concave 230 face 316 of the socket member 220 to form a cup shaped well or fluid reservoir. Since the ultrasonic transducer assembly 202 is positioned in contact with the ball joint 204, all or a portion of the ultrasonic transducer surface is maintained in close contact with the inside facing surface 322 of the flexible membrane 104.

In operation, the shoulder 232 formed by the socket member 220 is placed in contact with the subject. By positioning the shoulder 232 in contact with the subject, a cavity is formed between the ultrasonic transducer assembly 202 and the subject by the concave portion 230 of the socket member 220. In at least some instances, an acoustic coupling gel may be placed in the concave portion 230 of the socket member 220 such that the cavity between the ultrasonic sensor assembly 202 and the subject is filled by the acoustic coupling gel. The intimate contact between the ultrasonic transducer 202 and the flexible member 104 and the ability to fill the concave portion 230 with an acoustic gel may improve the quality of the resultant acoustic image data acquired by the ultrasonic transducer assembly 202. Beneficially, the presence of an acoustic coupling gel between the oscillating ultrasonic transducer assembly 202 and the subject tends to minimize discomfort of the subject and has been found particularly advantageous where the three-dimensional ultrasound based assessment device 100 is used in ophthalmologic applications.

An example first drive assembly 212 in the form of a permanent bar magnet 350 is depicted in FIG. 3. The bar magnet 350 may, in some instances, be coaxially aligned with the longitudinal axis of the elongated stem 206. In at least some implementations, the bar magnet 350 may be partially or completely embedded in or encapsulated by the elongated stem 206. For example, the bar magnet 350 can be placed centrally within an injection molded elongated stem 206, with one pole proximate one end of the elongated stem 206 (e.g., proximate ball joint 204) and the other pole proximate the other end (e.g., second end 210) of the elongated stem 206.

Figure 4C:
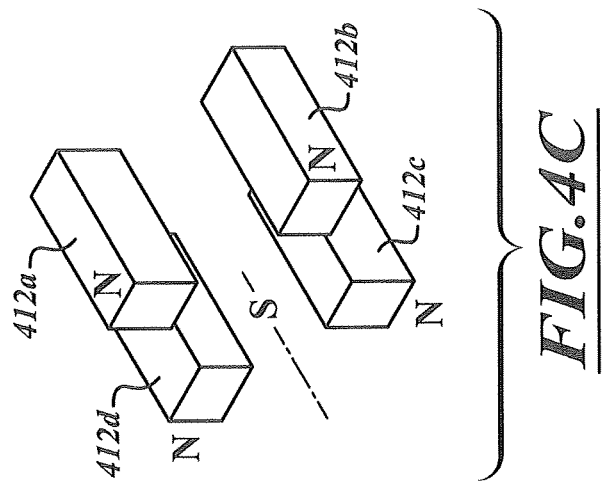
FIG. 4C is a perspective view of a first drive assembly in the form of a number of axial bar magnet sections that can be received by the elongated stem extending from the ball joint, according to one illustrated embodiment.

The second drive assembly 214 is disposed within the housing 102 at a location proximate at least a portion of the first drive assembly 212. For example the second drive assembly 214 can include eight sets of windings 214a-214h disposed within the housing 102 at a location proximate a pole (e.g., the NORTH pole) of the bar magnet 350. FIG. 4A shows another permanent magnet arrangement useful for providing some or all of the first drive assembly 212. In at least some instances, at least a portion of the first drive assembly 212 can include an annular or toroidal magnet 404. The toroidal magnet 404 can have a central aperture 406 and a planar or curved outer surface 408. In at least some instances, the second end of the elongated stem 206 may have a diameter less than the diameter of the central aperture 406, in which case, the toroidal magnet 404 can be positioned about the elongated stem 206. The outer diameter of the toroidal magnet 404 may be of any size, including a diameter that is less than, equal to, or greater than the outside diameter of the elongated stem 206. The toroidal magnet 404 has a radial magnetization, a first pole proximate the outer periphery or outer diameter and a second pole proximate an inner periphery or inner diameter (i.e., central aperture).

Figure 4B:
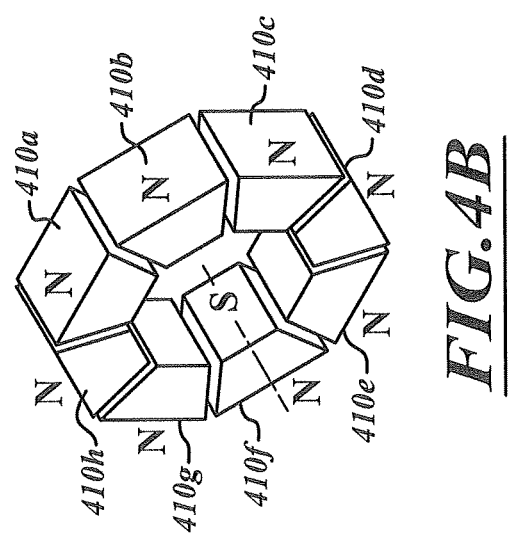
FIG. 4B is a perspective view of a first drive assembly in the form of a number of radial bar magnet sections that can be received by the elongated stem extending from the ball joint, according to one illustrated embodiment.
Figure 4A:
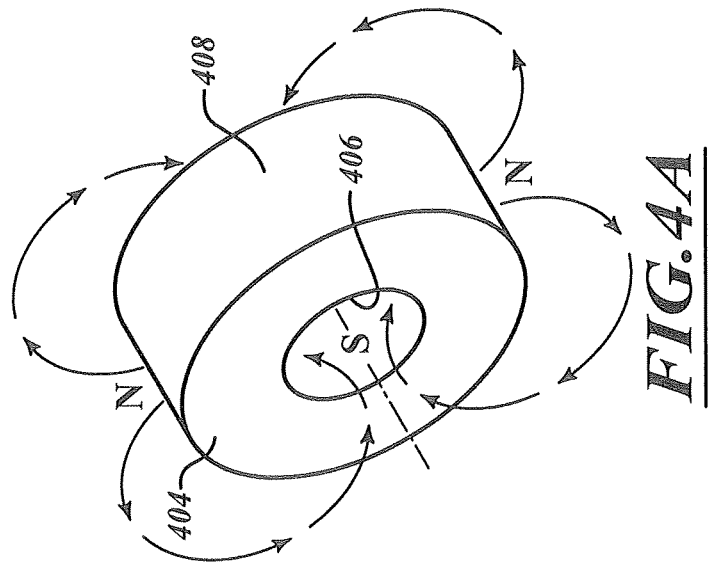
FIG. 4A is a perspective view of a first drive assembly in the form of a toroidal magnet that can be received by the elongated stem extending from the ball joint, according to one illustrated embodiment.

FIG. 4B shows another permanent magnet arrangement useful for providing some or all of the first drive assembly 212. In at least some instances, at least a portion of the first drive assembly 212 can include a number of individual arcuate permanent magnet sections 410a-410h (collectively, "arcuate permanent magnet sections 410"). Although eight arcuate permanent magnet sections 410 are shown in FIG. 4B, any number of arcuate permanent magnet sections 410 of similar or dissimilar shape may be used to provide some or all of the first drive assembly 212. In at least some instances, some or all of the arcuate permanent magnet sections 410 may be partially embedded or completely encapsulated by at least a portion of the elongated stem 206. In other instances, some or all of the arcuate permanent magnet sections 410 may be adhered or physically coupled to an exterior surface of the elongated stem 206. As with the toroidal magnet 404 (FIG. 4A), the arcuate permanent magnet sections 410 have a radial magnetization, a first pole proximate the outer periphery or outer diameter (i.e., convex surface) and a second pole proximate an inner periphery or inner diameter (i.e., concave surface).

FIG. 4C shows yet another permanent magnet arrangement useful for providing some of all of the first drive assembly 212. In at least some instances, the first drive assembly 212 can include a number of permanent bar magnets 412a-412d (collectively "permanent bar magnets 412") arranged on one or more axes parallel to the longitudinal axis of the elongated stem 206. Although four, evenly spaced, permanent bar magnets 412 are shown in FIG. 4C, any number of permanent bar magnet 412 of similar or dissimilar shape or spacing may be used to provide some or all of the first drive assembly 212. In at least some instances, some or all of the permanent bar magnets 412 may be partially embedded or completely encapsulated by at least a portion of the elongated stem 206. In other instances, some or all of the permanent bar magnets 412 may be adhered or physically coupled to an exterior surface of the elongated stem 206. As with the bar magnet 402 (FIG. 3), the permanent bar magnets 412 can be oriented with one pole proximate one end of the elongated stem 206 (e.g., proximate ball joint 204) and the other pole proximate the other end (e.g., second end 210) of the elongated stem 206.

Figure 5:
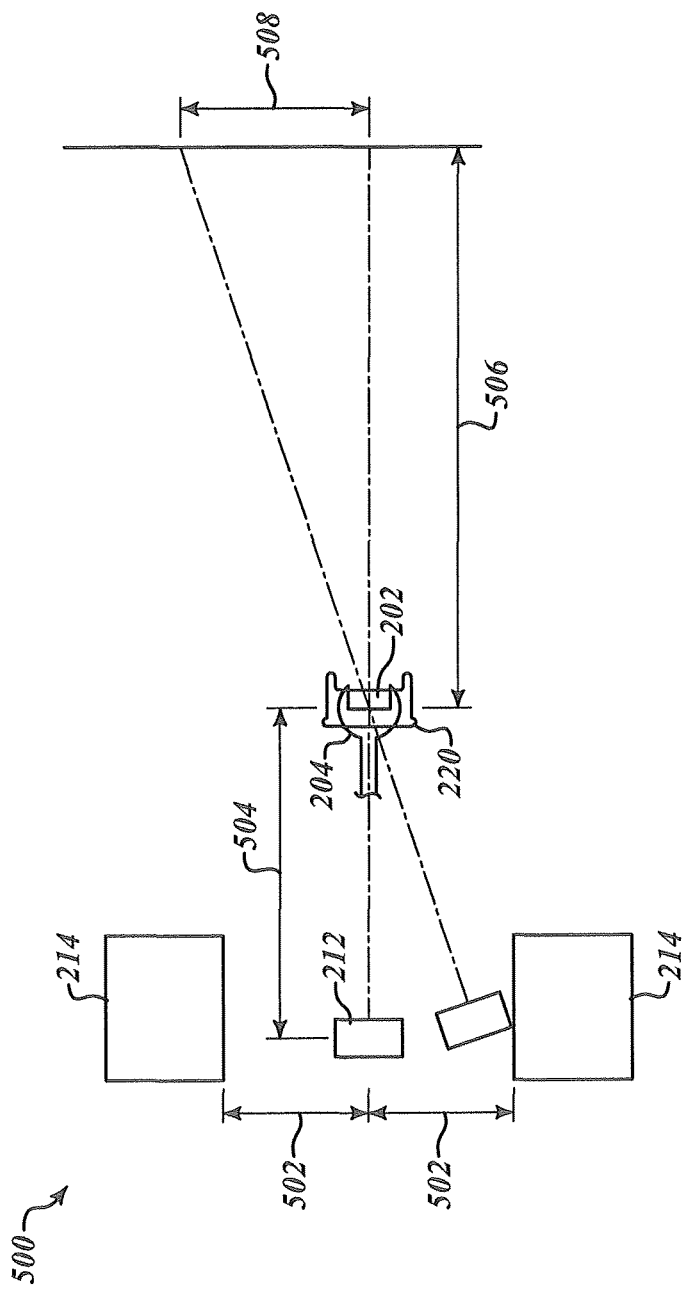
FIG. 5 is a schematic showing the possible displacement of the first drive assembly using the magnetic interaction of the first drive assembly with the second drive assembly, and the resultant displacement of the axial ultrasonic emission produced by the ultrasonic transducer assembly, according to one illustrated embodiment.

FIG. 5 shows an example ultrasonic emission pattern 508 achievable using the magnetic interaction between the first drive assembly 212 and the second drive assembly 214. In FIG. 5, the first drive assembly 212 is capable of oscillating within a radius 502. In at least some instances, controlling the shape and intensity of the magnetic field produced by the second drive assembly 214 can permit virtually any desired cone of coverage with the ultrasonic transducer assembly 202. As shown in FIG. 5, the ball joint 204 is used to provide a fixed pivot point within the socket member 220 about which the first drive assembly 212 and the ultrasonic transducer 220 rotate.

Thus, for ophthalmologic ultrasound, the minimum first drive assembly radius 502 permitting a complete scanning of the optic nerve sheath can be determined based on the generalized anatomy of the human eye, the target structure (i.e., optic nerve sheath) and distance from the target structure. The optic nerve is routed through the optic nerve sheath which enters the posterior portion of the eye at a location approximately opposite the lens which is positioned within the iris on the anterior portion of the eye. The average human eye has a depth of approximately 24 millimeters and an optic nerve sheath diameter of approximately 5 millimeters. Thus, the target area investigated using the ultrasonic transducer 202 is relatively small; located an axial distance 506 of from about 23 millimeters to 33 millimeters from the face of the ultrasonic transducer assembly 202 and having a radius of coverage 508 of about 3 to 6 millimeters. Thus, given the distance 504 between the face of the ultrasonic transducer assembly 202 and the first drive assembly 212, the first drive assembly radius 502 for ophthalmologic use can be determined.

Given the relatively shallow focus depth of the ultrasonic transducer, a carrier frequency less than that found in typical ophthalmologic use may be employed. The ultrasonic transducer assembly 202 can have a carrier frequency of from about 2 megahertz (MHz) to about 20 MHz; about 3 MHz to about 15 MHz; or about 5 MHz to about 10 MHz. In one example, an ultrasonic transducer assembly 202 having a fixed focus of approximately 27 millimeters and emitting a carrier frequency of about 8 MHz may be used to measure the optic nerve sheath diameter and globe depth of a typical human eye.

Figure 6:
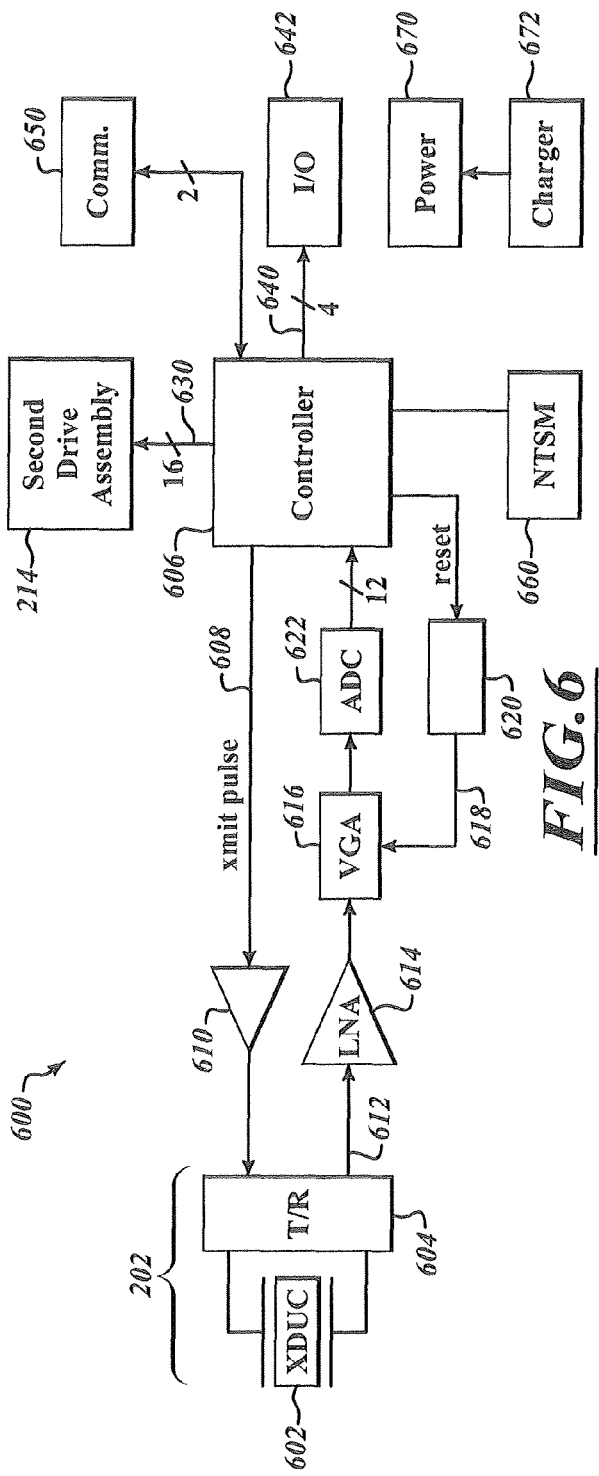
FIG. 6 is an electrical block diagram of a handheld three-dimensional ultrasound based assessment device, according to one illustrated embodiment.

FIG. 6 shows a schematic block diagram 600 of an example three-dimensional ultrasound based assessment device 100. The three-dimensional ultrasound based assessment device 100 depicted in FIG. 6 represents a pulse-echo system in which the transducer (e.g., a piezoelectric element) 602 is alternately placed in an active mode where energy is emitted for a first period of time followed by a passive mode where reflected energy returned from the subject is received for a second period of time. The ultrasonic transducer assembly 202 can include at least the transducer 602 and a communicably coupled transceiver 604. The ultrasonic transducer assembly 202 can be communicably coupled to a controller 606. The controller 606 generates at least one output signal 608 which passes through an amplifier 608 prior to receipt by the transceiver 604. The transceiver 604 stimulates one or more transducers 602 to emit a focused energy output at a frequency well above the threshold of human hearing.

The energy emitted by the ultrasonic transducer assembly 202 in the active mode enters the subject and is reflected by the various interfaces formed between structures in the target. At least a portion of the energy emitted by the transducer 602 during the active mode is returned to the transducer 602 during the passive mode. The transducer 602 converts the returned energy to an electrical signal that is provided to the transceiver 604.

The transceiver 604 generates a return signal 612 containing data indicative of one or more characteristics of the reflected sonic energy returned to the transducer 602. The return signal from the transceiver 604 is passed through one or more fixed or variable gain amplifiers prior to receipt by the controller 606. As shown in FIG. 6, in one or more instances, the return signal 612 passes through a first, fixed gain, low noise amplifier 614 followed by a second, variable gain, amplifier 616. In at least some instances, the controller 606 may alter, adjust or control the gain of the variable gain amplifier 616 using one or more control signals 618 provided by the controller 606. The amplified return signal 612 is converted to a digital signal using an analog to digital converter 622 to provide digital return signal as an input to the controller 606.

The controller 606 can include any number of systems, devices, or any combination of systems and devices suitable for controlling one or more operational aspects of the ultrasonic transducer assembly 202, for analyzing the acoustic image data provided by the ultrasonic transducer assembly 202, and for generating one or more output signals based at least in part on the acoustic image data provided by the ultrasonic transducer assembly 202. The controller 606 can include a microprocessor, application specific integrated circuit ("ASIC"), a digital signal processor ("DSP"), a programmable gate array ("PGA"), a field programmable gate array ("FPGA"), a reduced instruction set computer ("RISC") processor, or any other device having similar capabilities.

Recall that the interaction between the magnetic fields generated by the first drive assembly 212 and the second drive assembly 214 are used to move or "sweep" the ultrasonic transducer assembly 202 through a pattern to obtain three-dimensional acoustic image data of the target. The controller 606 can alter the shape or intensity of the magnetic field produced by the first drive assembly 212, the shape or intensity of the magnetic field produced by the second drive assembly 214, or the shape or intensity of both drive assemblies to achieve any desired sweep pattern with the ultrasonic transducer assembly 202 or frequency of oscillation.

In at least one instance, the controller 606 can directly or indirectly (e.g., through one or more intermediate controllers, for example a pulse width modulated or "PWM" controller—not shown in FIG. 6) selectively control all or a portion of the second drive assembly 214 to generate a composite magnetic field having any desired strength or intensity. For example, the controller 606 can selectively control current flow to all or a portion of the second drive assembly 214 such that the magnetic field produced by the second drive assembly 214 accurately positions the first drive assembly 212 at any desired location within the magnetic field produced by the second drive assembly 214. By selectively changing the flow of current to some or all of the second drive assembly 214, the controller 606 is able to displace the first drive assembly 212 to any desired location within the magnetic field produced by the second drive assembly 214. In at least some instances, the controller 606 can directly or indirectly generate a pulse width modulated control signal having a frequency in excess of the speed of motion of the elongated stem 206 that is useful to control the current flow to all or a portion of either (or both) the first drive assembly 212 or the second drive assembly 214.

The return signal 612 can include data representative of an acoustic image of the target structure(s). For example, in some instances, the return signal 612 can include data representative of an acoustic image of the optical nerve sheath and globe structures. Such acoustic image data can be processed by the controller 606 using one or more image processing techniques to identify and measure one or more structures present in the acoustic image data. For example, the controller 606 can execute one or more machine-executable instruction sets that permit the autonomous identification and measurement of the optic nerve sheath diameter. The machine-executable instructions may also cause comparison of the measured attributes or characteristics of anatomical structure to reference measurements of similar attributes or characteristics of reference anatomical structure. The machine-executable instructions may further cause provision of one or more output signals containing data representative or indicative of the measured optic nerve sheath diameter, the results of the comparison. Additionally or alternatively, the machine-executable instructions may cause production of one or more output signals containing data representative of an intracranial pressure that corresponds to the measured optic nerve sheath diameter. Such data can advantageously be used to detect conditions such as elevated intracranial pressure in a subject. In another example, the controller 606 can execute one or more machine-executable instruction sets that permit the autonomous identification and measurement of the globe depth to provide one or more output signals containing data representative of the measured globe depth. Such globe depth measurement data can advantageously be used to diagnose conditions such as a ruptured globe. Using the three-dimensional ultrasound based assessment device 100, such diagnoses can be made quickly by almost any user with or without training, without the need for invasive procedures, without exposing the patient to ionizing radiation or RF signals, and without having to wait for access to CT equipment and radiologists. With appropriate machine-executable instruction sets, the controller 606 can similarly autonomously identify and diagnose other ophthalmologic and non-ophthalmologic conditions.

Responsive to the autonomous determination of one or more measurements or similar diagnostic information, the controller 606 can generate one or more display output signals 640 that include data indicative of the measurement or diagnostic information. The controller 606 can communicate the one or more display output signals 640 to an input/output device ("I/O device") 642. In at least some instances, the I/O device 642 can include the display device 108 described in detail in FIGS. 1C and 1D. In at least one instance, the I/O device 642 can display a numeric value or one or more graphical elements that are indicative of or correspond to the determined measurements or similar diagnostic information. For example, the I/O device 642 can display the numeric values indicative of the determined optic nerve sheath diameter (e.g., 5.1 mm) or the determined globe depth (e.g., 26.0 mm). In other instances, rather than or in addition to displaying a value or graphical element, the I/O device 642 may display an indicator, for example a GREEN indicator indicative of a result within a defined acceptable limit and a RED indicator indicative of a result outside a defined acceptable limit. Such display devices can include, but are not limited to any current or future monochromatic or color display device such as a liquid crystal display (LCD), an electronic paper display, a light emitting diode (LED) display, or the like.

The I/O device 642 advantageously displays only a numeric value, text, symbol or graphical elements that are indicative of or correspond to the determined measurements or similar diagnostic information without any ultrasound images. However, the return signal 612 provided to the controller 606 includes data representative of the ultrasound or acoustic image of the target obtained by the ultrasonic transducer assembly 202. For example, the return signal 612 can include data representative of an ultrasound or acoustic image of the optic nerve sheath and globe. In some instances, the I/O device 642 may include a wired or wireless port to allow transfer or transmission of ultrasound or acoustic image data from the ultrasound based assessment device.

While a simple user interface is preferred, the I/O device 642 may optionally include one or more data input devices such as a microphone, keyboard, touch screen, cursor controller, device, or the like. Such data input devices may permit a greater degree of operator interaction with the three-dimensional ultrasound based assessment device 100. However, such comes at the cost of training and ease of use in fast moving, stressful or chaotic situations. In one implementation, the I/O device 642 may, for example, include a microphone capable of converting an audio input into one or more signals containing data representative of the audio input. In at least some implementations, the controller 606 can associate the signal containing the data representative of the audio input with a signal including data representative of the acoustic image to provide a "package" containing both audio and image data. Such may be useful, for example, in performing remote diagnoses where the acoustic image and oral observation and subject data are associated and transmitted to a remote location for analysis. Such may also be useful in an institutional setting where verbal subject identification data may be associated with acoustic image data for storage in and subsequent retrieval from a centralized database or similar data storage structure.

In another implementation, the I/O device 642 may include one or more machine readable code readers or scanners or RFID interrogators, readers or scanners. For example, the I/O device 642 may include at least one machine readable code scanning device capable of reading one-dimensional (e.g., barcode) and two-dimensional (e.g., QR code) machine readable symbols to provide a signal containing data indicative of the information contained in the machine readable symbol. In at least some instances, the controller 606 can associate the signal containing the data indicative of the information contained in the machine readable symbol or RFID transponder with a signal including data representative of the acoustic image to provide a "package" containing both machine readable code and image data. Such may be useful, for example, in an institutional setting where machine readable symbol data corresponding to a machine readable symbol on a particular subject's wristband may be associated with acoustic image data for storage and subsequent retrieval.

All or a portion of the acoustic image data provided to the controller 606 by the return signal 612 may be optionally transmitted to one or more external devices, systems, or networks via a wired or wireless communications interface 650. In at least one instance, the communications interface 650 can include a wireless interface capable of communicably coupling with one or more external systems, devices, or networks. For example, the communications interface 650 may include either or both a Bluetooth® interface or Universal Serial Bus (USB) interface that is capable of communicably coupling directly to a storage device, a handheld computing device, a laptop computer, a tablet computer, or a desktop computer. In some implementations, the communications interface 650 may include either or both an IEEE 802.11 (i.e., "WiFi") interface or cellular interface (e.g., global system for mobile communications "GSM," or CDMA) that is capable of communicably coupling to a remote network, storage, or computing device. In some instances, transfer of all or a portion of the acoustic image data via the communications interface 650 may be autonomously initiated by the controller 606 when one or more defined external systems, devices, or networks are communicably coupled to the three-dimensional ultrasound based assessment device 100. In other implementations, transfer of all or a portion of the acoustic image data via the interface 650 may be manually initiated by the user of the three-dimensional ultrasound based assessment device 100.

All or a portion of the ultrasound or acoustic image data provided to the controller 606 by the return signal 612 may optionally be stored in one or more non-transitory storage media 660. The one or more nontransitory storage media 660 may be variously present in the form of fixed nontransitory storage media, removable nontransitory storage media, or any combination thereof. Fixed nontransitory storage media 660 can include any type of non-removable volatile or non-volatile data storage in the three-dimensional ultrasound based assessment device 100. Example removable nontransitory storage media can include any current or future developed nontransitory data storage device. Example removable nontransitory storage media formats can include, but are not limited to, a Secure Digital ("SD") card, a microSD card, Memory Stick, Memory Stick Micro, or similar. In some instances, all or a portion of the nontransitory storage media 660 may be used to store or otherwise retain input data provided to the I/O device 642, including without limitations, data corresponding to one or more scanned machine readable codes, data corresponding to one or more audio inputs, or any combination thereof.

The three-dimensional ultrasound based assessment device 100 can be powered using one or more power sources 670. In some instances, the one or more power sources 670 can include one or more energy storage devices such as single use (i.e., disposable) batteries, rechargeable batteries, ultracapacitors, or the like. In some instances, the one or more power sources 670 may include an external or internal power converter that can be coupled to an electric grid, for example an adapter to convert alternating current power to direct current power (e.g., a wall mount AC adapter).

In some instances, the one or more power sources 670 may include one or more currently available or future rechargeable batteries or the like. Such rechargeable batteries can include, but are not limited to, nickel/cadmium cells, nickel/metal hydride cells, lithium ion cells, lithium ion polymer cells, and similar. In at least some instances, the three-dimensional ultrasound based assessment device 100 can include one or more built-in charging systems 672 capable of recharging the one or more power sources 670 without requiring removal of the one or more power sources 670 from the device 100. Such built-in charging systems 672 may include a non-contact charging circuit, for example an inductive charging circuit or similar.

Figure 7:
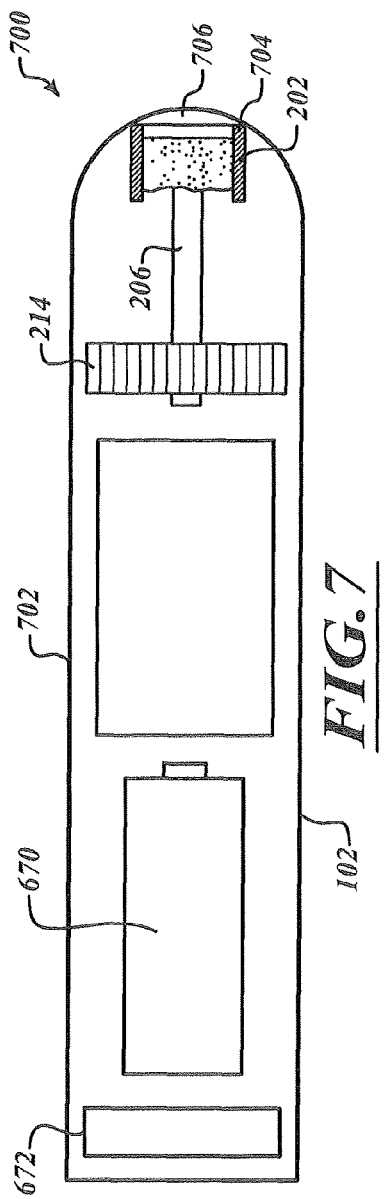
FIG. 7 is a partial cross section of a handheld three-dimensional ultrasound based assessment device showing a power source, an ultrasonic transducer assembly, an acoustical lens and an aluminum matching layer disposed between the ultrasonic transducer and the acoustical lens, according to one illustrated embodiment.

FIG. 7 shows another example three-dimensional ultrasound based assessment device 700 that includes a cylindrical tubular housing 702 with the ultrasonic transducer assembly 202 disposed proximate a convex, hemispherically shaped, flexible membrane 704. An acoustic lens 706 can be at least partially disposed between the face of the ultrasonic transducer assembly 202 and the flexible membrane 704. Also visible in FIG. 7 are one or more energy storage devices 670 and one or more built-in charging systems 672.

In contrast to the concave flexible member 104 used in conjunction with the three-dimensional ultrasound based assessment device 100 depicted in FIGS. 1A-1D, the convex flexible member 704 used with the three-dimensional ultrasound based assessment device 700 provides a surface that facilitates direct physical contact between the flexible member 704 and the subject to obtain acoustic image data. Such eliminates the need for an acoustic coupling gel or similar agent between the three-dimensional ultrasound based assessment device 700 and the subject.

In at least some implementations, when in operation the second drive assembly 214 sweeps or otherwise displaces the ultrasonic transducer 202 though one or more defined patterns to achieve a desired coverage of the target structure. In at least some implementations, the flexible membrane 704 accommodates the motion of the ultrasonic transducer assembly 202 while acoustic image data of the target structure is obtained.

Although heretofore described in the context of an ultrasonic transducer assembly 202 that is swept or otherwise displaced through a pattern by the magnetic interaction between the first drive assembly 212 and the second drive assembly 214, in some instances, a fixed ultrasonic transducer assembly 202 may be manually swept through a pattern to obtain acoustic image data of the target structure. In such instances, the controller 606 may provide the user with an audible indication, a visual indication or both an audible and a visual indication that sufficient acoustic image data of the target structure has been obtained. The convex shape of the portion of the three-dimensional ultrasound based assessment device 700 in contact with the subject can facilitate the "rocking" or "sweeping" motion of the ultrasonic transducer 202 on the subject to obtain acoustic image data.

In at least some instances, one or more systems, devices, or structures capable of measuring the movement of the three-dimensional ultrasound based assessment device 700 may be communicably coupled to the controller 606 when acoustic image data is obtained by manually sweeping the three-dimensional ultrasound based assessment device 700. In some instances, such devices may include a number of accelerometers, Doppler motion detectors, or similar motion sensing elements disposed at defined points in, on, or about the three-dimensional ultrasound based assessment device 700. For example, sensors may sense current passing through windings or coils positioned about an end of the stem, induced by magnets carried at the end of the stem, the currents indicative of movement of the stem relative to the windings or coils. Such would allow the controller 606 to determine the location and orientation of the device 700 in a three-dimensional space. Determining the location and orientation of the device 700 in a three-dimensional space enables the controller to 606 to map the acoustic image data provided by the ultrasonic transducer 202 into a single three dimensional image of the target area.

FIG. 8A shows a cross section of an example ultrasonic transducer assembly 202 disposed in a three-dimensional ultrasound based assessment device 700. FIG. 8B shows an enlarged cross-section of the ultrasonic transducer assembly 202 including an acoustic lens 706. The ultrasonic transducer 202 includes a frame 802, piezoelectric element 804, tube 806, backing material 808, and an optional acoustic lens 706. The frame 802 is formed of an electrically conductive material, for example a metal, for instance aluminum or steel. The frame 802 may generally have a cup shape, with a proximal end 812a and a distal end 812b. In use, the proximal end 812a is proximate the flexible membrane 104, 704, and the distal end 812b is attached to the three-dimensional ultrasound based assessment device 100, 700 electronics. For instance, the frame 802 may have a generally planar body portion 816 at the proximal end 812a, and a number of legs 818a, 818b (collectively "legs 818") which extend therefrom to define the distal end 812b. The legs 818 may be formed by tab portions 820a, 820b (see FIG. 8B) of the frame 802 which are bent out of a plane of the planar body portion 816, for example to be perpendicular thereto.

The piezoelectric element 804 may take any variety of piezoelectric elements commonly used in ultrasound transducers. The piezoelectric element 804 is typically generally planar having a front surface 822a and an opposed back surface 822b. The piezoelectric element 804 may, for example, take the form of a PZT-5A material, having a 4 MHz thickness and 10 mm diameter. The piezoelectric element 804 is polarized in the thickness mode. The piezoelectric element 804 is received by the frame 802, with the front surface 822a supported by the planar body portion 816 of the frame 802. The frame 802 provides electrically coupling between the front surface (i.e., one electrode) 822a of the piezoelectric element 804 and electrical traces on the ultrasonic transceiver 604, for example providing a ground to the piezoelectric element 804.

The tube 806 is formed of an electrically conductive material, for example a metal, for instance brass. The tube 806 contains the backing material 808, and provides electrical connection of the back surface (i.e., one electrode) 822b of the piezoelectric element 804 to the ultrasonic transceiver 604, for example providing the signal thereto and/or therefrom. While the tube 806 can be any type of electrical conducting material, ½ hard H58 tempered brass also known as alloy 260 has shown to be suitable, providing desired characteristics. The tube 806 may, for example, have an outer diameter (OD) of approximately 7/16" and an inner diameter (ID) of approximately 3/8". Such may advantageously minimize a percentage of the piezoelectric element 804 covered by the tube 806 when using conventional commercially available piezoelectric elements.

The backing material 808 may take any of a large variety of forms. For example, various epoxies and polyvinyl chloride (PVC) polymers may be used as fillers, mixed with microspheres or other particles designed to scatter and break up the ultrasound in the backing layer. Tungsten powder can be added to increase a density of the backing material to adjust an acoustical impedance thereof.

In at least some implementations, an optional acoustic lens 706 may be disposed proximate the ultrasonic transducer. While the acoustic lens 706 may take a variety of forms, an acrylic lens has proven suitable. The acoustic lens 706 may, for example, take the form a ½" radius convex lens which focuses the ultrasound. Thus, in some implementations, the three-dimensional ultrasound based assessment device 700 may employ two acoustical matching layers, the first formed by the frame (e.g., aluminum body portion) 802 of the ultrasonic transducer 202 and the second formed by the acoustic lens 706. The frame (e.g., aluminum) matching layer advantageously performs two functions, acting as a matching layer and providing an electrical connection the front surface of the piezoelectric element 804.

FIG. 8C shows the frame 802, according to one illustrated embodiment. The frame 802 may include the generally planar body portion 116, with a pair of opposed tabs 820a, 820b (collectively "tabs 820") extending therefrom, which may be bent out of plane, for example perpendicularly thereto. While only a single bend is shown for each, the tabs 820 may have multiple bends. The frame 802 may include one or more other features to provide a mechanically compliant connection which would allow greater movement of the piezoelectric element 804 when excited. All the layers of the ultrasonic transducer assembly 202 may be fused together, for example with a thin layer of adhesive and cured under pressure to allow the surface roughness of the materials to create an electrical contact.

Figure 9A:
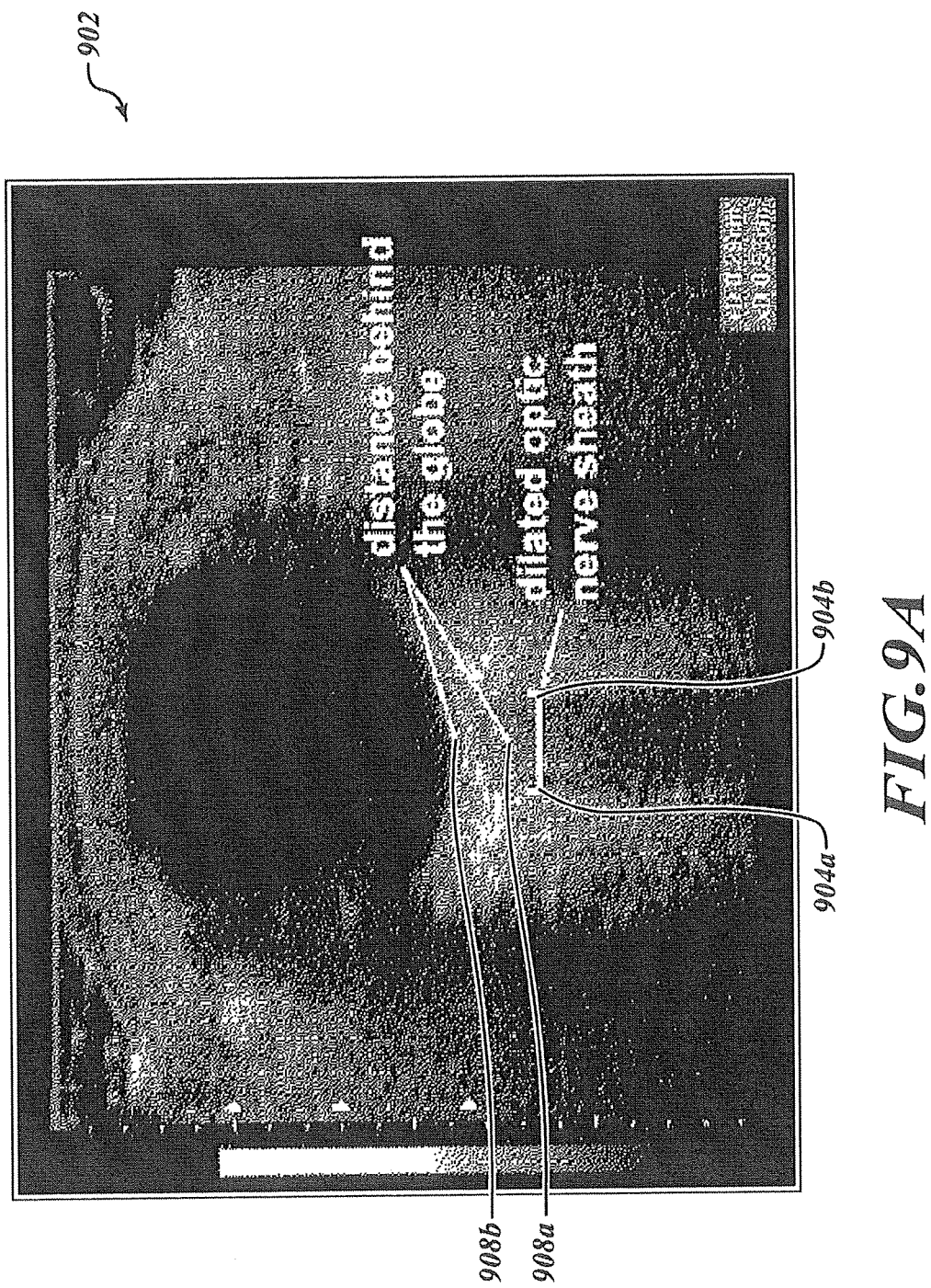
FIG. 9A is an ultrasound showing an acoustic image of a human eye cross section, also showing a measurement of an optic nerve sheath diameter of a dilated optic nerve sheath, according to one illustrated embodiment.
Figure 9B:
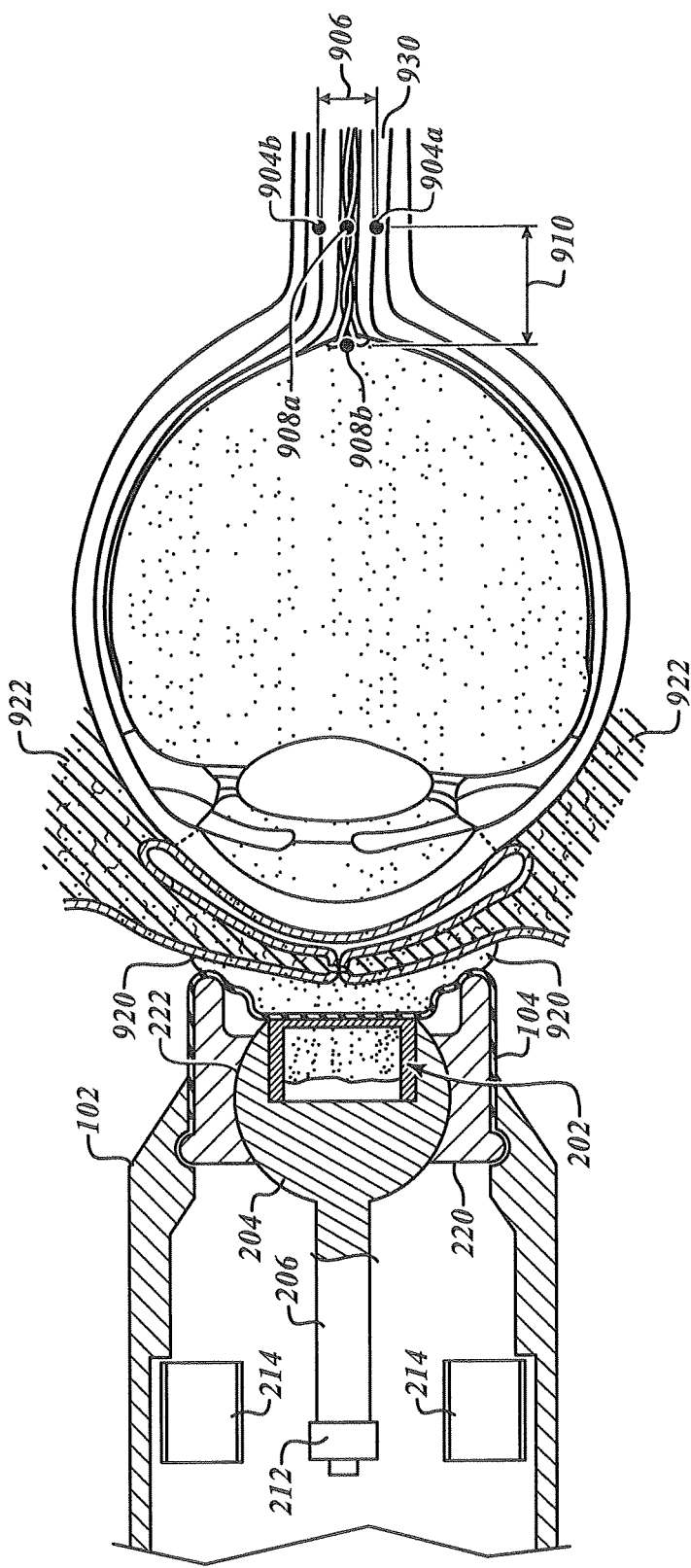
FIG. 9B is a cross section showing the measurement of an optic nerve sheath diameter using the three-dimensional ultrasonic based assessment shown in FIGS. 1A-1D, according to one illustrated embodiment.

FIGS. 9A and 9B shows an example ophthalmologic use of the three-dimensional ultrasound based assessment device 100 to measure an optic nerve sheath diameter of a subject. FIG. 9A provides an example acoustic image 902 generated by the acoustic image data collected by the three-dimensional ultrasound based assessment device 100. In at least some implementations, one or more image processing algorithms executed by the controller 606 can identify a number of reference points on structures in the target area scanned by the ultrasonic transducer assembly 202. For example, one or more image processing algorithms executed by the controller 606 can identify a number of points 904a-904b on the optic nerve sheath (collectively "optic nerve sheath diameter points 904") and a number of points 908a-908b determining the depth of the optic nerve sheath diameter points 904 behind the eye globe (collectively "optic nerve sheath diameter depth points 908"). Such optic nerve sheath diameter points 904 and optic nerve sheath diameter depth points 908 may be used by the controller 606 to determine the optic nerve sheath diameter 906 at a given depth 910 behind the eye globe. The controller 606 can generate one or more signals to display a numeric value corresponding to the optic nerve sheath diameter 906 (e.g., 5.25 mm) on the display 108. The measured optic nerve sheath diameter 906 can be used to provide an indication of whether a subject is suffering from an elevated intracranial pressure condition. Such a diagnosis may advantageously be made without the use of an invasive procedure and without the use of ionizing radiation, with minimal or no training or waiting for access to equipment or radiologists.

Although described in the context of obtaining an optic nerve sheath diameter, other ophthalmologic measurements, including but not limited to: globe depth, globe volume, intracranial pressure may be similarly directly or indirectly determined using the three-dimensional ultrasound based assessment device 100 or the three-dimensional ultrasound based assessment device 700.

To obtain such a measurement using the three-dimensional ultrasound based assessment device 100, the cavity 230 formed in the flexible membrane 104 is at least partially filled with an acoustic coupling gel 920. The gel filled flexible membrane 104 is then placed into contact with the outer surface of the subject's eyelid 922. The three-dimensional ultrasound based assessment device 100 is activated by the user and, in response, the controller 606 causes current to flow through either or both the first drive assembly 212 or the second drive assembly 214. The interaction of the magnetic fields produced by the first drive assembly 212 and the second drive assembly 214 cause the displacement or movement of the elongated stem 206 in either a defined or random pattern. The displacement of the elongated stem 206 causes the ball joint 204 to rotate within the ball joint socket 222. As the ball joint 204 rotates, the beam of sound energy emitted by the ultrasonic transducer 202 is swept through a generally conical pattern that includes at least a portion of the target (i.e., the optic nerve sheath 930 on the posterior portion of the eye).

The acoustic image data acquired by the ultrasonic transducer 202 is compiled into a composite three-dimensional image by the controller 606. Through the use of one or more image processing machine executable codes, the controller 606 identifies a number of optic nerve sheath diameter points 904 on the optic nerve sheath 930. The controller 606 then uses some or all of the number of optic nerve sheath diameter points 904 to determine the optic nerve sheath diameter 906. The controller 606 can generate a signal including data indicative of the determined optic nerve sheath diameter 906 which can be displayed as a numeric value, text, symbol, or graphical element on the display 118.

In some instances, the controller 606 may optionally save or otherwise store some or all of the acoustic image data providing the acoustic image 902 on a nontransitory storage media 660. In some instances, the controller 606 may optionally communicate some or all of the acoustic image data providing the acoustic image 902 to one or more external displays, computing, or data storage devices via the communications interface 650.

The various embodiments described above can be combined to provide further embodiments.

To the extent that they are not inconsistent with the teachings herein, the teachings of: U.S. patent application Ser. No. 12/948,622 filed Nov. 17, 2010; U.S. provisional patent application Ser. No. 61/573,493 filed Sep. 6, 2011; U.S. provisional patent application Ser. No. 61/621,877 filed Apr. 9, 2012; U.S. provisional patent application Ser. No. 61/638,925 filed Apr. 26, 2012; U.S. provisional patent application Ser. No. 61/638,833 filed Apr. 26, 2012; and are U.S. provisional patent application Ser. No. 61/725,893 filed Nov. 13, 2012; each incorporated herein by reference in their entirety. Aspects of the embodiments can be modified, if necessary to employ concepts of the various patents, applications and publications to provide yet further embodiments.

These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

The invention claimed is:

1. A handheld ultrasound based assessment device, comprising:
    a housing having a front end, a back end, and a cavity, the front end having an opening that opens into the cavity having a primary axis;
    a flexible membrane that at least in use is disposed across the opening at the front end of the housing, the flexible membrane having an inside facing surface that faces an interior of the housing and an outside facing surface that faces an exterior of the housing;
    an ultrasound transducer assembly having an outward face via which ultrasound signals are transmitted and received;
    an elongated stem having a first end extending rearwardly toward the back end of the housing from the ultrasound transducer assembly and a second end received in the cavity of the housing;
    a first drive assembly mechanism physically coupled to the elongated stem at least proximate the second end of the elongated stem;
    a second drive assembly mounted within the housing at least proximate the second end of the elongated stem, the first and the second drive assembly mechanisms magnetically interacting to cause a displacement of the ultrasound transducer assembly at least during use;
    a socket member that includes a ball joint socket located at least proximate the first end of the housing; and a ball joint from which the elongated stem extends rearwardly toward the back end of the housing, the ball joint pivotally received in the ball joint socket of the socket member, the ultrasound transducer assembly mounted to the ball joint for movement therewith.

2. The handheld ultrasound based assessment device of claim 1 wherein the ultrasound transducer assembly is adhered directly to the inside facing surface of the flexible membrane without any intervening structures.

3. The handheld ultrasound based assessment device of claim 1 wherein the flexible membrane is a thermoplastic elastomer has at least one circular relief contour.

4. The handheld ultrasound based assessment device of claim 1 wherein the flexible membrane has at least one shoulder portion proximate a radial periphery of the flexible membrane and has a circular relief contour spaced radially inward from the shoulder.

5. The handheld ultrasound based assessment device of claim 1 wherein the socket member comprises a first portion and a second portion, the second portion complimentary to the first portion to be physically mated thereto during assembly of the socket member.

6. The handheld ultrasound based assessment device of claim 5 wherein the flexible membrane physically elastically retains the first and the second portions of the socket member together.

7. The handheld ultrasound based assessment device of claim 5 wherein the socket member is body of revolution with a central passage, and is mounted in the opening of the housing.

8. The handheld ultrasound based assessment device of claim 7 wherein the socket member further comprises a radial flange sized to be received in a groove in the opening in the housing.

9. The handheld ultrasound based assessment device of claim 5 wherein the elongated stem is an integral unitary portion of at least one of the first or the second portions of the ball joint.

10. The handheld ultrasound based assessment device of claim 1 wherein the first drive assembly mechanism includes one or more permanent magnets and the second drive assembly mechanism includes at least two windings.

11. The handheld ultrasound based assessment device of claim 1 wherein the first drive assembly mechanism includes a radially polarized annular magnet disposed about the second end of the elongated stem, the radially polarized annular magnet including one or more segments.

12. The handheld ultrasound based assessment device of claim 1, further comprising:
a single visual indicator device carried by the housing; and
a control subsystem housed by the housing and communicatively coupled to control operation of an ultrasound transducer of the transducer assembly, and communicatively coupled to the visual indicator device and operable to cause the visual indicator device to provide at least one of a number, a text character, a graphic, a color or a symbol as a visual indicator indicative of at least one of a measurement of an anatomical structure or a comparison of the measurement of the anatomical structure with a reference, without providing any image of the anatomical structure.

13. The handheld ultrasound based assessment device of claim 12 wherein the visual indicator is a number indicative of the measure of an optic nerve sheath diameter.

14. The handheld ultrasound based assessment device of claim 12, further comprising:
a radio coupled to the control subsystem and operable to at least transmit information externally from the handheld ultrasound based assessment device.

15. A handheld ultrasound based assessment device, comprising:
a housing having a front end, a back end, and a cavity, the front end having an opening that opens into the cavity having a primary axis;
a flexible membrane that at least in use is disposed across the opening and positioned at the front end of the housing, the flexible membrane having an inside facing surface that faces an interior of the housing and an outside facing surface that faces an exterior of the housing;
an ultrasound transducer assembly having an outward face via which ultrasound signals are transmitted and received;
an elongated stem having a first end and a second end, the first end of the elongated stem extending rearwardly from the ultrasound transducer assembly in the cavity toward the back end of the housing;
a first drive assembly mechanism physically coupled to the elongated stem at least proximate the second end of the elongated stem; and
a second drive assembly mounted within the housing at least a portion of which is proximate the second of the elongated stem, the first and the second drive assembly mechanisms magnetically interacting to cause a displacement of the ultrasound transducer assembly at least during use,
wherein the ultrasound transducer assembly is attached to the inside facing surface of the flexible membrane to conically pivot about the primary axis of the housing without any hinges or any other attachments.

16. The handheld ultrasound based assessment device of claim 15 wherein a portion of the ultrasound transducer assembly is adhered to a portion of the inside facing surface of the flexible membrane.

17. The handheld ultrasound based assessment device of claim 15, further comprising:
an acoustic lens received between the outward face of the ultrasound transducer assembly and the flexible membrane.

18. The handheld ultrasound based assessment device of claim 15 wherein the flexible membrane is an integral unitary portion of the housing.

19. The handheld ultrasound based assessment device of claim 15 wherein the second drive assembly mechanism includes at least two windings.

20. The handheld ultrasound based assessment device of claim 15 wherein the first drive assembly mechanism includes a single rod permanent magnet, with a first pole proximate the second end of the elongated stem and the second pole space from the second end of the elongated stem.

21. The handheld ultrasound based assessment device of claim 15 wherein the first drive assembly mechanism includes a radially polarized annular magnet disposed about the second end of the elongated stem, the radially polarized annular magnet including one or more segments.

22. The handheld ultrasound based assessment device of claim 21 wherein the visual indicator is a number indicative of a measure of an optic nerve sheath diameter.

23. The handheld ultrasound based assessment device of claim 21, further comprising:
a radio coupled to the control subsystem and operable to at least transmit information externally from the handheld ultrasound based assessment device.

24. The handheld ultrasound based assessment device of claim 15, further comprising:
- a single visual indicator device carried by the housing; and
- a control subsystem housed by the housing and communicatively coupled to control operation of an ultrasound transducer of the transducer assembly, and communicatively coupled to the visual indicator device and operable to cause the visual indicator device to provide at least one of a number, a text character, a graphic, a color or a symbol as a visual indicator indicative of at least one of a measurement of an anatomical structure without providing any image of the anatomical structure or a comparison of the measurement of the anatomical structure with a reference.

25. A handheld ultrasound based assessment device, comprising:
- a housing having a front end, a back end, and a cavity, the front end having an opening that opens into the cavity having a primary axis;
- a flexible membrane that at least in use is disposed across the opening at the front end of the housing;
- an ultrasound transducer assembly having a face;
- an elongated stem having a first end and a second end, the first end of the elongated stem extending rearwardly from the ultrasound transducer assembly in the cavity toward the back end of the housing;
- a first drive assembly mechanism comprising one or more permanent magnets disposed radially about the elongated stem at least proximate the second end; and
- a second drive assembly comprising a plurality of windings positioned radially about the cavity and radially spaced from one another to form a passage sized to receive the second end of the elongated stem with the permanent magnets to cause a displacement of the transducer assembly at least during use.

26. The handheld ultrasound based assessment device of claim 25, further comprising:
- a control subsystem housed by the housing and communicatively coupled to control operation of an ultrasound transducer of the transducer assembly and communicative coupled to control a current flow through the windings.

27. The handheld ultrasound based assessment device of claim 26, further comprising:
- a single visual indicator device carried by the housing, and wherein the control subsystem is further communicatively coupled to the visual indicator device and operable to cause the visual indicator device to provide at least one of a number, a text character, a graphic, a color or a symbol as a visual indicator indicative of at least one of a measurement of an anatomical structure without providing any image of the anatomical structure or a comparison of the measurement of the anatomical structure with a reference.

28. The handheld ultrasound based assessment device of claim 27 wherein the visual indicator is a number indicative of a measure of an optic nerve sheath diameter, without any image of the anatomical structure displayed by the control subsystem.

29. The handheld ultrasound based assessment device of claim 26, further comprising:
- a radio coupled to the control subsystem and operable to at least transmit ultrasound image data externally from the handheld ultrasound based assessment device.

30. A handheld ultrasound based assessment device, comprising:
- a housing having a front end, a back end, and a cavity, the front end having an opening that opens into the cavity having a primary axis;
- a flexible membrane that at least in use is disposed across the opening at the front end of the housing;
- an ultrasound transducer assembly having a face, the ultrasound transducer assembly proximate the front end;
- an elongated stem having a first end extending rearwardly toward the back end of the housing from the ultrasound transducer assembly and a second end;
- a first drive assembly mechanism coupled to the elongated stem at least proximate the second end;
- a second drive assembly mounted within the housing the first drive assembly mechanism and the second drive assembly, magnetically interacting to cause a displacement of the ultrasound transducer assembly at least during use;
- a single visual indicator device carried by the housing; and
- a control subsystem housed by the housing and communicatively coupled to control operation of an ultrasound transducer of the transducer assembly, communicative coupled to control a current flow through the windings, and communicatively coupled to the visual indicator device and operable to cause the visual indicator device to provide at least one of a number, a text character, a graphic, a color or a symbol as a visual indicator indicative of at least one of a measurement of an anatomical structure or a comparison of the measurement of the anatomical structure with a reference.

\* \* \* \* \*

UNITED STATES PATENT AND TRADEMARK OFFICE
CERTIFICATE OF CORRECTION

| | | |
|---|---|---|
| PATENT NO. | : 8,672,851 B1 | Page 1 of 1 |
| APPLICATION NO. | : 13/800993 | |
| DATED | : March 18, 2014 | |
| INVENTOR(S) | : William Quirk et al. | |

It is certified that error appears in the above-identified patent and that said Letters Patent is hereby corrected as shown below:

In the Claims

Column 32, Line 31:
"a second drive assembly mounted within the housing the" should read, --a second drive assembly mounted within the housing, the--.

Signed and Sealed this
Twelfth Day of August, 2014

Michelle K. Lee
*Deputy Director of the United States Patent and Trademark Office*